US012778620B2

(12) United States Patent
Park

(10) Patent No.: US 12,778,620 B2
(45) Date of Patent: Nov. 3, 2026

(54) TOOL SET FOR PERCUTANEOUS EXTRAFORAMINOTOMY AND METHOD OF PERFORMING PERCUTANEOUS EXTRAFORAMINOTOMY USING SAME

(71) Applicant: Kyung-Woo Park, Seoul (KR)

(72) Inventor: Kyung-Woo Park, Seoul (KR)

( * ) Notice: Subject to any disclaimer, the term of this patent is extended or adjusted under 35 U.S.C. 154(b) by 131 days.

(21) Appl. No.: 18/645,385

(22) Filed: Apr. 25, 2024

(65) Prior Publication Data

US 2025/0281199 A1 Sep. 11, 2025

(30) Foreign Application Priority Data

Mar. 8, 2024 (KR) ........................ 10-2024-0032976

(51) Int. Cl.

| | |
|---|---|
| ***A61B 17/3205*** | (2006.01) |
| ***A61B 17/00*** | (2006.01) |
| ***A61B 17/32*** | (2006.01) |
| ***A61B 17/34*** | (2006.01) |

(52) U.S. Cl.

CPC .... *A61B 17/32053* (2013.01); *A61B 17/3403* (2013.01); *A61B 2017/00893* (2013.01); *A61B 2017/320052* (2013.01)

(58) Field of Classification Search

CPC .......... A61B 17/32053; A61B 17/3403; A61B 2017/320052; A61B 17/3472; A61B 17/320708; A61B 17/3401; A61B 17/3417; A61B 17/3421; A61B 2017/00261; A61B 2017/0046; A61B 2017/00477

USPC ....................................... 606/246–249, 86 A

See application file for complete search history.

(56) References Cited

U.S. PATENT DOCUMENTS

| | | | | |
|---|---|---|---|---|
| 1,248,492 A * | 12/1917 | Hill | A61B 17/34 604/165.02 |
| 4,573,448 A * | 3/1986 | Kambin | A61B 17/3417 606/179 |
| 2006/0089633 A1* | 4/2006 | L. Bleich | A61B 17/32002 606/32 |
| 2007/0066987 A1* | 3/2007 | Scanlan | A61B 17/3472 600/564 |

(Continued)

FOREIGN PATENT DOCUMENTS

| | | |
|---|---|---|
| JP | 2008-508943 A | 3/2008 |
| JP | 2010-502305 A | 1/2010 |

(Continued)

*Primary Examiner* — Eduardo C Robert
*Assistant Examiner* — Tara Rose E Carter
(74) *Attorney, Agent, or Firm* — IP&T GROUP LLP

(57) ABSTRACT

Disclosed are a tool set for percutaneous extraforaminotomy and a method of performing percutaneous extraforaminotomy using the same. The tool set includes: a stylet member including an elongated probe, a guide pipe, a cap, and a hub body; a trocar including a needle and a first handle; a cannula including a sleeve, a fixation shaft, and a handle; and a curette including a rod, a resection tip, and a second handle. According to the tool set and method, in the procedure in which the tools of the tool set percutaneously penetrate the muscle layer and reach a transforaminal ligament resection-target point of intervertebral foramen, it is possible to improve the directional property and straightforward property of the tools, and during ligament resection, it is possible to facilitate direction switching.

8 Claims, 14 Drawing Sheets

(56) References Cited

U.S. PATENT DOCUMENTS

| | | | | |
|---|---|---|---|---|
| 2009/0216234 | A1* | 8/2009 | Farr | A61B 90/50 604/264 |
| 2010/0185161 | A1* | 7/2010 | Pellegrino | A61B 17/3421 604/272 |
| 2018/0110531 | A1* | 4/2018 | Arthurs | A61B 17/1635 |

FOREIGN PATENT DOCUMENTS

| | | | | |
|---|---|---|---|---|
| JP | 2013-516292 | A | 5/2013 | |
| KR | 10-0627170 | B1 | 9/2006 | |
| WO | WO-2012102842 | A1 * | 8/2012 | A61B 17/32053 |
| WO | 2021/106923 | A1 | 6/2021 | |

* cited by examiner

FIG. 4(prior art)

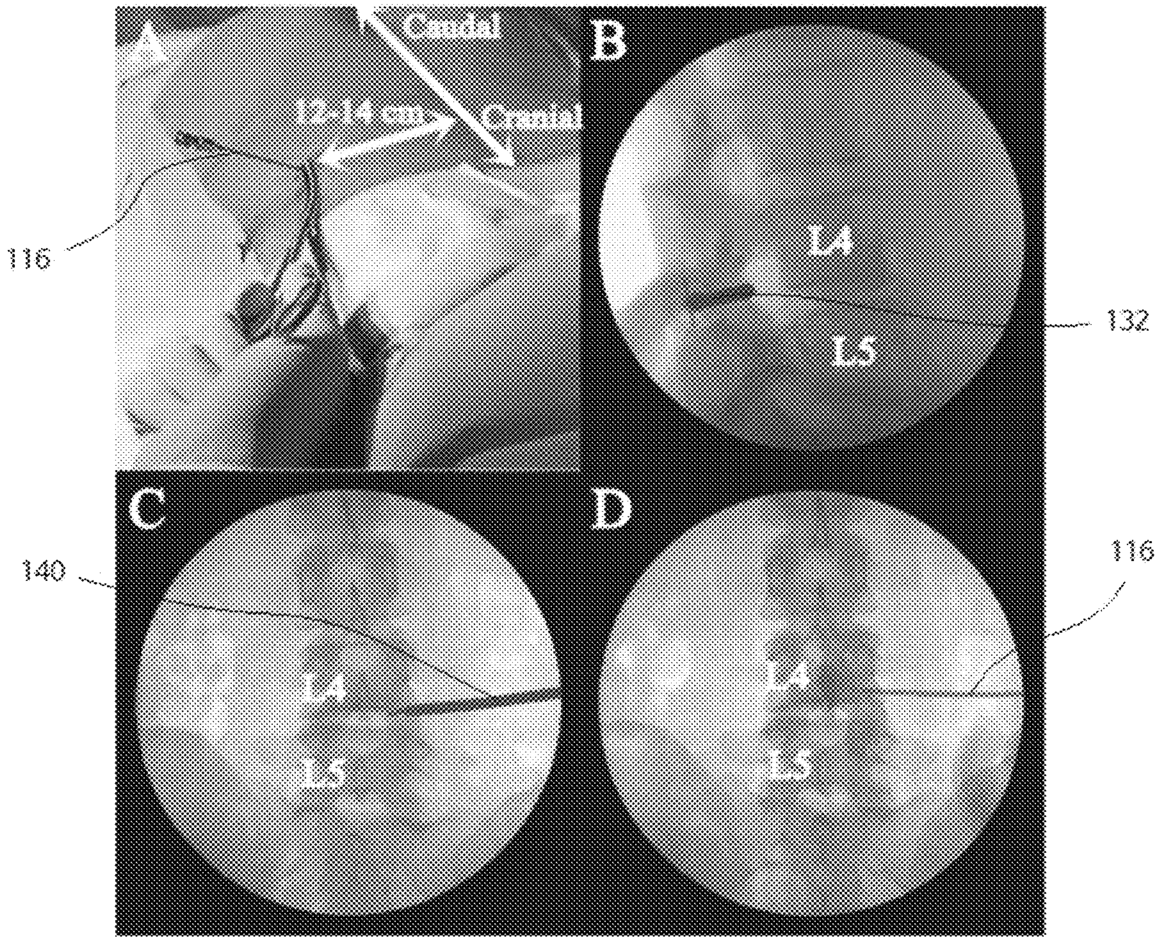

Fluoroscopic images during lumbar extraforaminotomy procedures. A) Entry point of the needle is 12-14cm away from the midline of the vertebral body. B) In the lateral fluoroscopic view, the cannula tip is advanced until it is located at the posterior part of the borderline between the inferior and superior articular processes. C) A distraction of the foraminal ligament and mechanical adhesiolysis are performed by the curette through the cannula until the tip of the curette reaches the medial border of the pedicle in the anteroposterior fluoroscopic image. D) Postadhesiolysis epidurogram is obtained before injecting local anesthetics and corticosteroids (Figure 2D).

TOOL SET FOR PERCUTANEOUS EXTRAFORAMINOTOMY AND METHOD OF PERFORMING PERCUTANEOUS EXTRAFORAMINOTOMY USING SAME

CROSS-REFERENCE TO RELATED APPLICATION

This application claims priority under 35 U.S.C. § 119 to Korean Patent Application No. 10-2024-0032976 filed on Mar. 8, 2024, which is incorporated herein by reference in its entirety.

TECHNICAL FIELD

The present invention relates to a tool set for expanding the intervertebral foramen so that an inflammatory substance existing in the spinal canal may be smoothly discharged out of the intervertebral foramen and a pain-relieving medicine may be injected into the intervertebral foramen, and a method of performing percutaneous extraforaminotomy using the tool set. More particularly, the present invention relates to a tool set for percutaneous extraforaminotomy and a method of performing percutaneous extraforaminotomy using the same. According to the tool set and method of the present invention, in the procedure in which tools, including a stylet member, a trocar, a cannula, and a curette, percutaneously penetrate the skin and the muscle layer, reach a target point for ligament resection, and then remove minute ligament entangled in the intervertebral foramen, it is possible to allow the tools to reach the target point for ligament resection within a short time by improving the directional property and straightforward property of the tools, it is possible to facilitate the ligament resection by enhancing the steering property (direction switching when peeling off the ligament), and it is possible to enhance the safety of the procedure by minimizing a gap between the cannula and the curette.

BACKGROUND ART

Typically, lumbar extraforaminotomy is a surgical procedure for removing the cause of back pain and leg pain, caused by nerve compression by intervertebral foramen narrowing or spinal canal narrowing, by expanding the narrowed nerve passageway by peeling off the ligament entangled in the intervertebral foramen and then injecting a pain-relieving medicine.

As of now, various articles have provided an anatomical description of the transforaminal ligaments (TFL) of the lumbar spine and many authors have conducted the radiological analysis of the transforaminal ligaments. Even if the authors discussed the possible clinical implications of these ligaments, it is unclear what clinical implications of these ligaments are. In particular, the influence of the transforaminal ligament (TFL) has been insignificant to the surgeons who focus on the mechanical factors such as disc bulging, ligament thickening, facet hypertrophy, and structural changes like stenosis and spondylolisthesis.

On the other hand, it is quite reasonable to presume that any situation which diminishes the size of the intervertebral foramen, such as stenosis or reduction of intervertebral disc height, would increase the relative amount of area in the foramen occupied by the transforaminal ligaments. However, the study and analysis regarding t clinical significance of this is presently not sufficient.

The article—Jun-Hong Min, et. al. "anatomic analysis of the transforaminal ligament in the lumbar intervertebral foramen" operative neurosurgery Vol. 57(1):37 to 41, 2005.—provides an anatomical description of the transforaminal ligaments of the lumbar spine. Although the importance of these structures is not yet clear, they may contribute to reducing physical pressure on the nerve roots in certain cases. Spine surgeons should be aware of the presence of these structures and need to consider anatomical structures in the etiology of otherwise unexplained sciatic symptoms.

The article introduced above is an excellent and timely article in evaluating the anatomical analysis of the transforaminal ligaments of the lumbar intervertebral foramen, because the posterolateral approach is becoming more popular for the surgical treatment of lumbar far-lateral discs and foraminal stenosis.

Even if surgeons regarding general spinal treatment usually do not search for transforaminal ligaments during posterior foraminotomy, it is important and also useful for surgeons to have anatomical information in this area. If the authors could study the correlation between the anatomical structure and the surgical structure of the intervertebral foramen through the radiological analysis of the transforaminal ligaments in the near future, it will be of great value and informative for neurosurgeons.

The intervertebral foramen by clinical anatomy consists of the spinal nerves (the dorsal root ganglion (DRG)), the sinuvertebral nerves, the intervertebral veins, the radicular vein, the artery, and the ligament flavum.

FIG. 1 is a view illustrating a distribution of ligaments around the intervertebral foramen. As illustrated in FIG. 1, the ligaments around the intervertebral foramen are categorized into ligaments of the entrance zone, ligaments of the mid-zone, ligaments of the exit zone, and ligaments of the post-canal zone. The ligaments of the entrance zone consist of the posterior longitudinal ligament, the Hoffmann ligament, and the peridural membrane. The ligaments of the mid-zone consist of the fascial condensations attaching the nerve root sleeve to the pedicles, and the ligamentum flavum. The ligaments of the exit zone (around the intervertebral foramen) consist of the internal ligament, the transforaminal ligament, and the external ligament. The ligaments of the post-canal zone consist of the cribriform fascia.

The role of the foraminal ligament in the induction of low back pain including sciatica is divided into two aspects: inflammatory aspect and mechanical aspect. In terms of the inflammatory aspect, low back pain is affected by a series of processes such as activation of fine and non-myelinated pain endings, release of proinflammatory cytokines, vasodilation and edema, and adhesive fibrosis. In terms of the mechanical aspect, the below conditions should be considered: malposition of the transarticular ligament (especially, superior and inferior corporotransverse ligament) due to acquired reduction of intervertebral disc height, ossification of foraminal ligament, anomalies of trunks, and entrapment of dorsal root ganglia (DRG) (L5: corporotransverse ligament, L1 to L4: inferior corporotransverse ligament).

Whereas the chemical neurolysis is applied to the problems of the inflammatory aspect, the mechanical epidural neurolysis by caudal catheterization or percutaneous extraforaminotomy is used to solve the problems of the mechanical aspect.

Back pain is a very common symptom that most people experience more than once for the whole life. It is known that from 70 to 80 percent among the patients with back pain can be improved through the conservative method without a special treatment. The cases accompanying sciatica account for 13 to 40 percent of the patients with back pain. Pathophysiological reason of sciatica is divided into a mechanical factor and a biochemical factor. In point of fact, we have neurosurgically put emphasis on mechanical factors such as disc bulging, ligament thickening, and facet hypertrophy for the treatment of sciatica. That is, most of neurosurgeons have believed that mechanical problems such as disc herniation and spinal stenosis cause sciatica, much more back pain. However, as a result of conducting a study on the epidural neurolysis, the applicant for the present invention has found that an inflammatory reaction around the intervertebral foramen is the main cause of sciatica.

FIG. 2 is a schematic view illustrating an image for explaining the process of pain and nerve dysfunction. Referring to FIG. 2, the process of pain and nerve dysfunction may be understood.

As illustrated in FIG. 2. Step A shows that adhesion molecules in the endoneurial capillary are activated by tumor necrosis factor (TNF).

In Step B, Sub-step 1) depicts adhesion of circulating white blood cells (WBC). Sub-step 2) depicts extravasation of white blood cells. Sub-step 3) depicts aggregation of thrombocytes and formation of a thrombus.

In Step C, Sub-step 1) depicts local release of tumor necrosis factor (TNF), myelin injury, damage to natrium channels, and induction of allodynia in dorsal root ganglion (DRG) and spinal cord. Sub-step 2) depicts decreased blood flow and increased permeability nutritional deficit.

In other words, biochemical factors undetected by magnetic resonance imaging (MRI) such as insufficient blood supply to nerve, mild inflammation, and fibroblastic adhesion around intervertebral foramen play a more important role as factors causing pain and nerve dysfunction.

So far, however, the surgery for treating pain of disc patients has relied on neurosurgical treatment of mechanical factors rather than analysis of biochemical factors which are not checked by MRI.

Meanwhile, a surgical tool set widely used for extraforaminotomy or for decompression of lumbar herniated intervertebral discs is disclosed U.S. Pat. No. 4,573,448. As illustrated in FIG. 3, a conventional surgical tool set for extraforaminotomy includes a sleeve 112, a probe 116, a guide wire 118, a trocar 120, a cannula 132, and a curette 140. The sleeve 112 is formed to have a pointed inclined tip at one side in such a manner as to penetrate the skin muscle layer of a patient and to reach a ligament resection-target point of the intervertebral foramen, and includes a Luer lock fitting 114 at the other end. The probe tip 116 is inserted into the sleeve 112 through the Luer lock fitting 114. The guide wire 118 is inserted into the probe tip 116. The trocar 120 is formed in such a manner that one end portion thereof, which comes into contact with the ligament of the intervertebral foramen, serves as a blunt tip and that an adapter 128 having a Luer lock fitting 130 is mounted to the other end portion. The trocar 120 reaches a ligament resection-target point of the intervertebral foramen under the guidance of the guide wire 118 inserted into the trocar 120 and secures a space for injecting anesthetic or contrast dye. The cannula 132 has a greater diameter than the trocar 120 and is inserted into the trocar 120. The cannula 132 performs a function of absorbing fragments of the ligament. The curette 140 is formed in the shape of a hollow cylinder in such a manner that the cannula 132 is inserted thereinto. The curette 140 has a grip 144 mounted to one end portion and has a Luer lock fitting 146 mounted to the other side, in such a manner as to peel off the ligament entangled in the intervertebral foramen by applying a twisting force to the end, at the proximal end of the tool.

To secure a peeling-off space of a ligament resection-target point of the intervertebral foramen sufficiently, the surgical tool set described above is configured so that the guide wire 118, the probe tip 116, the trocar 120, the curette 140, and the cannula 132, which penetrate locally, are in order of increasing diameter. That is, an inclined tip, having a pointed end portion, of the sleeve 112 enters percutaneously, and the probe tip 116 is inserted through the Luer lock fitting 114 of the sleeve 112, which penetrates the muscle layer and is located at the ligament resection-target point of the intervertebral foramen. At this time, the probe tip 116 is used to check whether the sleeve 112 is properly arranged or not. When the sleeve 112, properly arranged, comes into contact with the ligament of the intervertebral foramen, the probe tip 116 is drawn out and the guide wire 118 is inserted with the Luer lock fitting 114 for performing insertion of needle. In this state, the sleeve 112 is separated and the guide wire 118 is enabled to pass through in a twisted manner until the trocar 120 reaches the location of the intervertebral foramen. In this manner, in a process of guiding the trocar 120 toward the ligament resection-target point of the intervertebral foramen, the guide wire 118 properly guides the trocar 120 toward the ligament resection-target point while avoiding the nerves in such a manner as not to come into contact with the nerves distributed along with the ligament. When the trocar 120 is properly located, the guide wire 118 is removed, and the cannula 132 is enabled to pass through in a state of being inserted into the trocar 120. When the cannula 132 is arranged at its predetermined location, the trocar 120 is removed, and the curette 140 is inserted. Then, the ligament located at the ligament resection-target point of the intervertebral foramen is resected. The ligament peeled off through the resection operation is pulled out of the cannula 132 using forceps (not illustrated).

The surgical tool set described above is posterior-laterally inserted to reach the ligament resection-target point of the intervertebral foramen in a locally penetrating manner, and since a passageway to the intervertebral foramen is secured by the method that the tools are inserted in order of increasing diameter, the nerve root can be prevented from being damaged while the probe tip 116 is inserted.

However, through the above surgical tool set, it is significantly difficult to fulfill the local-penetrating process of the sleeve 112, the probe tip 116, and the guide wire 118 performed pre-emptively in order to properly position the trocar 120 at the target point. That is, the sleeve 112, the probe tip 116, and the guide wire 118 are in the shape of a very elongated needle. In addition, the local penetration of the sleeve 112, the probe tip 116, and the guide wire 118 is performed with them gripped only by the tip of the surgical operator's fingers. For this reason, it takes a lot of force for them to percutaneously penetrate the muscle layer and reach the ligament resection-target point. Furthermore, while direction switching is performed only with the force of the surgical operator's fingers, it is very difficult to precisely position the trocar 120 at the target point. This means that it is very difficult to perform a resection of the ligament spanning from the outer surface of the facet joint to the epidural space in order to create a tunnel passing through the intervertebral foramen from the outside to the inside (the epidural space).

FIG. 4 shows fluoroscopic images during intervertebral foramen ligament resection. The images in FIG. 4 are an excerpt from the following research paper: Sang Chul Lee, et. al., "Effectiveness of Percutaneous Lumbar Extraforaminotomy in Patients with Lumbar Foraminal Spinal Stenosis: A Prospective, Single-Armed, Observational Pilot Study" Pain Medicine 2017; Vol 18(10): 1975-1986.

Image (A) in FIG. 4 depicts that the entry point of the probe 116 is 12 cm to 14 cm away from the mid-line of the vertebral body and that a surgical operator who intends to enable the probe tip 116 to enter or intends to capture an image using a C-arm or the like enables the probe tip 116 to enter or captures an image while holding onto the probe tip 116 by a forcep. It can be seen that this process of percutaneously penetrating the muscle layer through local penetration and reaching the target point is very difficult. Image (B), which is a lateral view, illustrates that the tip of the cannula 132 advances until it is located at the posterior part of the borderline between the inferior and superior articular processes. Image (C) illustrates that the curette 140 inserted into the cannula 132 detaches the ligament until the tip of the curette 140 reaches the medial border of the pedicle in the anteroposterior (AP) view and performs the mechanical adhesiolysis. Image (D) illustrates that the post-adhesiolysis epidurogram is obtained before injecting the local anesthetics and corticosteroids.

To overcome the problems with extraforaminotomy that is performed using the above-described conventional surgical tool, the applicant for the present application has proposed a surgical tool for percutaneous extraforaminotomy based on the intervertebral foramen ligament resection (see U.S. Pat. No. 9,649,129). As illustrated in FIG. 5, the surgical tool for percutaneous extraforaminotomy, which is disclosed in U.S. Pat. No. 9,649,129, includes a trocar 202, a cannula 204, an end mill 206, and a curette 208. The trocar 202 serves to penetrate the skin and enter the intervertebral foramen. The cannula 204 includes a sleeve 214 having a handle 212 and a hollow guide space 214*a*, and reaches a target location for resection of the ligament within the intervertebral foramen, with the trocar 202 being inserted into the cannula 204. The end mill 206 includes a handle 216 and a blade tip 218 integrally mounted at a front end thereof, is inserted into the cannula 204, and scratches out the fine ligaments occluding the intervertebral foramen. The curette 208 is inserted into the cannula 204 and has a handle 220 at one end thereof and a concave scrapper tip 222 at the front end. The curette 208 additionally removes the scratched ligaments attached to the spinal facet joint and scrapes the residue.

Likewise, the surgical tool with the structure described above also has the trocar 202 in the shape of a slender needle. Thus, while holding onto the trocar 202 with the finger tips, the surgical operator experiences significant difficulty in enabling the trocar 202 to locally penetrate the muscle layer to reach the ligament resection-target point. Furthermore, in some cases, the trocar 202 is bent while penetrating the muscle layer for insertion. Accordingly, it is very difficult to properly seat the trocar 202 at its predetermined location.

A tissue modification device is disclosed in U.S. Pat. No. 9,456,829 and Japanese Patent Application Publication No. 2010-502305. In these patents, as illustrated in FIG. 6, a guide member 316 is inserted into an introducer device 314 penetrating the spinal facet joint. A body 308 to which a blade 310 for peeling off the ligament is mounted passes through the guide member 316. The body 308 is brought into contact with the ligament portion within the intervertebral foramen, and then is exposed out of the spinal facet joint. In these patents, the blade 310 peels off the ligament on the process of moving the body 308 by the operations of a handle 304 and an actuator 306, which are included in the introducer device 314.

In the tissue modification device, which has a structure as described above, while the body 308 is caused to move leftward and rightward, the blade 310 causes friction against the ligament within the intervertebral foramen, thereby peeling off the ligament. However, it is difficult to accurately position the body 308 at a complicatedly entangled portion within the intervertebral foramen. Furthermore, while the ligament is removed by the friction caused by the leftward and rightward movement of the body 308, there is a risk that the adjacent nerve tissues will be damaged.

In addition, a system and a method for treating spinal stenosis are disclosed in U.S. Patent Application Publication No. 2011/0288553. An instrument for use in medical surgery, which has a handle and extends along a common axis, is disclosed in U.S. Patent Application Publication No. 2008/0195084.

DOCUMENTS OF RELATED ART (Patent Document 1) U.S. Pat. No. 4,573,448 (issued on Mar. 4, 1986)

(Patent Document 2) U.S. Pat. No. 9,649,129 (issued on May 16, 2017)

(Patent Document 3) U.S. Pat. No. 9,456,829 (issued on Oct. 4, 2016)

(Patent Document 4) Japanese Patent Application Publication No. 2010-502305 (published on Jan. 28, 2010)

(Patent Document 5) U.S. Patent Application Publication No. 2011/0288553 (published on Nov. 24, 2011)

(Patent Document 6) U.S. Patent Application Publication No. 2008/0195084 (published on Aug. 14, 2008)

(Non-patent Document 1)) Jun-Hong Min, et. al., "anatomic analysis of the transforaminal ligament in the lumbar 2005, intervertebral foramen" operative neurosurgery Vol. 57 (1): 37 to 41

(Non-patent Document 2) Sang Chul Lee, et. al., "Effectiveness of Percutaneous Lumbar Extraforaminotomy in Patients with Lumbar Foraminal Spinal Stenosis: A Prospective, Single-Armed, Observational Pilot Study" Pain Medicine 2017; Vol 18 (10): 1975-1986.

DISCLOSURE

Technical Problem

Therefore, the present invention has been proposed in order to solve the above-mentioned problems, and an object of the present invention is to provide a tool set for percutaneous extraforaminotomy, which may improve the straightforward property and directional property of tools for extraforaminotomy, including a stylet member, a trocar, a cannula, and a curette, by using the respective handles, in the procedure in which the tools percutaneously penetrate the muscular layer and reach a transforaminal ligament resection-target point of the intervertebral foramen, and may facilitate direction switching (steerable property) during ligament resection.

Another object of the present invention is to provide a tool set for percutaneous extraforaminotomy, which may reduce hemorrhaging and maximize the safety of the surgical procedure, in the procedure in which tools for extraforaminotomy percutaneously penetrate the muscle layer in first and second resection operations, reach a transforaminal ligament resection-target point of the intervertebral foramen, and perform a resection of the transforaminal ligament.

Still another object of the present invention is to provide a tool set for percutaneous extraforaminotomy, which is capable of reliably reaching a ligament resection-target point at an accurate entry angle from the spinal facet joint during an introduction process of advancing to the ligament of the intervertebral foramen, by fundamentally enhancing a grip feeling of tools, including a stylet member, a trocar, and a cannula, not simply holding onto the tools with surgical operator's finger tips.

Yet another object of the present invention is to provide a method of performing percutaneous extraforaminotomy using a tool set for percutaneous extraforaminotomy, which allows a stylet member of the tool set to accurately reach a ligament resection-target point of the intervertebral foramen in a first process, and is capable of stably performing a second introduction process in which a trocar advances to the ligament resection-target point of the intervertebral foramen, and a resection process of resecting a ligament spanning from the ligament resection-target point to the epidural space.

Still yet another object of the present invention is to provide a method of performing percutaneous extraforaminotomy using the above-described tool set, which is capable of restoring a disc height and, at the same time, widening the space of the intervertebral foramen by filling a disc space with a hydrogel, thereby increasing the effectiveness of uninterrupted extraforaminotomy and relieving acute pain at an initial stage of the surgical procedure.

Technical Solution

According to one aspect of the present invention, there is a provided a tool set for percutaneous extraforaminotomy, including: a stylet member including an elongated probe, a guide pipe into which the probe is insertable and from which the probe is separable, a cap mounted to the probe, and a hub body mounted to the guide pipe and coupled to the cap, wherein the stylet member reaches a target point for resection of transforaminal ligament during the percutaneous extraforaminotomy; a trocar including a needle having a groove formed in a predetermined portion thereof and a needle tip with a pointed front end, and a first handle inserted into the needle and serving to apply a force to the needle in accordance with the angle of percutaneous entry to a spinal facet joint, wherein the trocar reaches the target point for resection of the transforaminal ligament under guidance of the guide pipe of the stylet member and drills a hole in the transforaminal ligament, during the percutaneous extraforaminotomy; a cannula including a sleeve formed to have a greater diameter than the trocar and having an axial through-hole into which the trocar is insertable, a fixation shaft located in a central portion of the cannula to insert and fix one end of the sleeve, and a handle having a seating portion formed on a rear surface thereof, wherein the cannula reaches the target point for resection of the transforaminal ligament under the guidance of the trocar during the percutaneous extraforaminotomy; and a curette including a rod which is inserted into the sleeve of the cannula, a resection tip provided at a front end of the rod and serving to peel off the transforaminal ligament at the target point for resection of the transforaminal ligament, scrape the residue of the transforaminal ligament resected primarily, and push the residue into the intervertebral foramen, and a second handle which is seated on the seating portion of the cannula.

In one embodiment of the present invention, the end of the probe of the stylet member and the end of the guide pipe each have a bevel cut and a curved portion formed by machining a lower portion opposite to the bevel cut in a round shape. The above structure serves to enable the curved portions to be inserted toward the target point while minimizing damage to the tissue, when coming into contact with the nerves or other critical tissues during entry into the intervertebral foramen.

In one embodiment of the present invention, the stylet member may have a handle configured by coupling a locking lever mounted to the cap to a locking groove formed in the hub body. In addition, a plurality of grooves may be formed in an outer circumferential surface of each of the cap of the stylet member and the hub body, so that the weight of the stylet member may be prevented from being biased toward the cap and a feeling of gripping may be enhanced, thereby stably administrating a contrast dye or a medicine through the hub.

In one embodiment of the present invention, the first handle of the trocar includes: a body having a lengthwise groove formed in the central portion thereof and an accommodation space formed in a one-side surface thereof to have a predetermined depth; a stepped portion formed at a rear end of the body and serving to provide a gripping force to a surgical operator; a shaft inserted into the accommodation space; and a lever having a pressing portion formed in a round shape to provide a pressing force while coming into contact with the groove of the needle, wherein the shaft is inserted into a center of the pressing portion and is rotated within the accommodation space to lock and unlock the needle.

In one embodiment of the present invention, the first handle of the trocar further includes a direction indicating surface formed as a flat surface on an upper surface of a front-end portion of the body in such a manner that the surgical operator applies a force to the direction indicating surface using a thumb, wherein the direction indicating surface serves as a reference surface for an entering angle of the needle.

In one embodiment of the present invention, the body further includes: coupling grooves formed on both sides of a seating portion; and finger-joint grooves formed on both sides of the fixation shaft and serving to enhance a feeling of gripping when the surgical operator's finger joints are placed therein.

In one embodiment of the present invention, a predetermined section at a front-end side of the sleeve of the cannula consists of a tapered portion with a gradient, and the reception tip having a gradient corresponding to the gradient of the tapered portion is exposed out of the tapered portion.

In one embodiment of the present invention, the tapered portion of the sleeve and the end of the resection tip of the curette may be coupled with little or no a gap therebetween.

In one embodiment of the present invention, the curette includes coupling protrusions on both sides of the second handle, wherein the coupling protrusions are inserted into the coupling grooves of the seating portion so that the handle of the cannula and the second handle of the curette are integrally coupled to each other.

In one embodiment of the present invention, the resection tip of the curette has a central concave portion to scrape the transforaminal ligament entangled in the intervertebral foramen, and a round-shaped rim portion formed at the periphery of the concave portion.

In one embodiment of the present invention, the resection tip of the curette has a straight section in such a manner as to come into close contact with an inner surface of the tapered portion of the sleeve, and is inserted into and protrudes from the tapered portion of the sleeve, and a gap between the end of the resection tip and the tapered portion has an allowable tolerance ranging from a transition fit to a clearance fit.

In one embodiment of the present invention, the rim portion formed at the resection tip of the curette has a rounded end.

The present invention also provides a method of performing percutaneous extraforaminotomy using a tool set for percutaneous extraforaminotomy, the method including: a first step of examining various ligaments around intervertebral foramen; a second step of determining an insertion location of a stylet member and a trocar according to a ligament structure around the intervertebral foramen, which is different among patients; a third step of inserting the stylet member toward a target point for resection through the skin of a portion (spinal facet joint) adjacent to the intervertebral foramen; a fourth step of identifying a location of the stylet member by injecting a contrast dye; a fifth step of restoring a disc height by filling a disc space with a hydrogel; a sixth step of inserting the trocar toward a target point for ligament resection under guidance of a guide pipe of the stylet member; a seventh step of performing a first resection operation; an eighth step of inserting the trocar into a cannula and then separating the trocar to secure a space for inserting subsequent tools; a ninth step of performing a second ligament resection operation using a curette coupled to the cannula; and a tenth step of inserting a catheter into the intervertebral foramen, suitably delivering a chemical substance to the periphery of nerve branches causing pain, and then discharging an inflammatory substance existing in the intervertebral foramen along with the chemical substance through the expanded intervertebral foramen.

In one embodiment of the present invention, the fifth step includes filling the disc space with the hydrogel through the guide pipe of the stylet member.

Advantageous Effects

According to the embodiments of the present invention, which are configured as described above, the following effects can be achieved.

First, since the stylet member, which enters primarily to find a ligament resection-target point of the intervertebral foramen, includes a probe and the guide pipe, a guide pipe can be prevented from being blocked by tissue, when a stylet member percutaneously penetrates the muscle layer and is inserted up to a target point on the spinal facet joint. A cap in the shape of a mortar is mounted at an end portion of the probe, and a hub body is mounted to the guide pipe, forming grooves in the cap and the hub body. Thus, these features maximize the feeling of gripping of surgical operator and can apply a predetermined force to the stylet member. Accordingly, when the stylet member is percutaneously inserted, the straightforward property and the directional property are enhanced. Thus, the stylet member can be inserted up to the target point on the spinal facet joint in an accurate targeting manner within a short time, and hemorrhaging can be reduced. In addition, the probe and the guide pipe are formed in such a manner that respective end portions have an inclined surface and each end portion is curved. As a result, since the curved portions come into contact with the nerves or other critical tissues in the entering process, damage to the tissue during insertion can be minimized.

Second, since the weight of a handle is reduced by half due to grooves, spaced at a predetermined distance apart from each other, that is formed in respective outer circumferential surfaces of the cap and a hub, the center of weight of the stylet member can be adjusted, preventing a phenomenon of excessive leaning toward the handle side and maintaining overall weight balance. Consequently, a contrast dye or a medicine can be stably injected without the stylet member being shaken. In addition, after the probe and the guide pipe together reach the ligament resection-target point, only the probe can be separated, and a contrast dye can be injected into the epidural space through the hub. Thus, a medicine can be injected toward a correct location in a state where the location of the tip of the guide pipe does not deviate from the ligament resection-target point.

Third, the effectiveness of uninterrupted extraforaminotomy can be increased by restoring a disc height by filling a disc space with a hydrogel and simultaneously widening a space of the intervertebral foramen. That is, while the intervertebral foramen is widened, a buckling portion of a capsule surrounding the spinal facet joint stretches out, and the surface of the spinal facet joint becomes smooth. As a result, during a subsequent ligament resection process, when the ligament around the spinal facet joint is peeled off in a scanning manner, from the entry point on the superior articular process through the surface of the spinal facet joint toward the inferior articular process, the process of resecting and peeling off the ligament can be easily and rapidly performed, thereby shortening the surgical procedure time. In addition, since the ligament resection process is enabled to be performed more accurately and safely, the nerve swelling as well as the frequency and duration of nerve contact that unavoidably occurs in a ligament resection process can be reduced. Therefore, acute pain due to nerve swelling immediately after extraforaminotomy can be minimized, and the effect of the extraforaminotomy can be increased.

Fourth, when percutaneously entering up to the target point of the spinal facet joint, since a trocar may be inserted up to a ligament resection-target point of the spinal facet joint along the guide pipe of the stylet member already placed on the target point of the spinal facet joint, the trocar can reach the ligament resection-target point relatively more easily than when the trocar enters without any guide. As a result, the preparation process for resection can be performed very simply and rapidly.

Fifth, since the trocar includes an elongated needle including a first handle with a lever for locking and unlocking the needle, the first handle enables the trocar to precisely aim from the spinal facet joint to the ligament resection-target point.

Sixth, since the first handle of the trocar enhances the surgical operator's feeling of gripping, the percutaneously entering process of the trocar during a primary resection procedure can be readily performed in a state in which the angle of entry is accurately adjusted. Particularly, with the first handle, it is easy to apply a force to the needle, so that the needle can penetrate the muscle layer without any deviation in the entry angle and can be accurately and straightly inserted up to the ligament resection-target point of the intervertebral foramen.

Seventh, as a direction indicating surface is formed on the first handle of the trocar, it may maintain the reference for direction when the needle enters percutaneously. Thus, even if the entry angle deviates, the angle of entry may be easily corrected.

Eighth, by integrating a second handle of the curette and a handle of the cannula, the steerable property (switchable directional property) can be enhanced when the ligament around the spinal facet joint is peeled off from the entry point on the superior articular process through the surface of the spinal facet joint toward the inferior articular process. Due to this enhanced steerable property, the ligament can be rapidly and accurately peeled off along the surface of the spinal facet joint.

Ninth, since the gap at the junction between the ends of the cannula and the curette can be minimized, in cases of anomaly that the lumbar arteriole is located at a specific location, the rupture of the lumbar arteriole, which occurs due to the location of the lumbar arteriole on a passageway for the ligament resection for extraforaminotomy, can be prevented in advance. Thus, the surgical procedure can be stably performed. As a result, the occurrence of complications such as retroperitoneal hematoma can be minimized.

Tenth, as the gap at the junction between the cannula and the curette is minimized, it is possible to minimize damage to the dorsal root ganglion caused by the reason that the dorsal root ganglion is caught in the gap during ligament resection for extraforaminotomy.

Eleventh, the risk of damage to the dura mater can be minimized by flattening the sharply formed upper and front surfaces of the tip of the curette, thereby ensuring the safety of the surgical procedure. That is, in the related art, while the curette moves backward and forward, a lateral blade and a sharply pointed front blade of the curette perform a ligament resection. In contrast, according to the present invention, a wide and round rim portion of the curette resects the ligament in a scanning manner as if the curette peeled off the ligament from downward to upward. Thus, when the curette penetrates the ligament and enters the epidural space, the risk of damage to the dura mater can be minimized, thereby ensuring the safety of the surgical procedure.

Twelfth, since a minimally invasive surgical procedure can be performed under local anesthesia, the surgical procedure time can be shortened, and the ligament resection-target point can be accurately identified by injecting a contrast dye. Accordingly, in one surgical procedure, tools for extraforaminotomy can be successively and sequentially introduced to the lesion sites in various intervertebral foramens to perform a resection of the ligament. As a result, through one surgical procedure, multilevel extraforaminotomy targeting the multi-joint intervertebral foramen is possible.

Thirteenth, since as a minimally invasive surgical procedure is performed under local anesthesia and the ligament is resected within a short surgical procedure time, the surgical procedure that uses the tools for extraforaminotomy can also be performed on an aged patient, a diabetic patient, or a patient having an underlying cardiovascular disease, such as hypertension or coronary artery disease.

DESCRIPTION OF DRAWINGS

FIG. 4 shows fluoroscopic images illustrating a process of performing intervertebral foramen ligament resection.

FIG. 11 illustrates a state where a pressing portion of a lever is separated from a groove in a probe tip, thereby unlocking the probe tip. FIG. 12 illustrates a state where the pressing portion of the lever presses against the groove in the probe tip, thereby locking the probe tip.

FIG. 13 is referenced to describe the straightforward property, the directional property, and the steerable property (switchable directional property) of the trocar.

FIG. 20A is a cross-sectional view illustrating a state where the tapered portion of the cannula and the resection tip are coupled to each other according to the related art of FIG. 19. FIG. 20B is a cross-sectional view illustrating that the resection tip of the curette is coupled to the tapered portion of the cannula according to the present invention shown in FIG. 18.

FIG. 23 illustrates the case where the lumbar arteriole is located posterior to the dorsal root ganglion (refer to a bold black circle in the central portion of the left-side figure), unlike in the typical distribution in which the lumbar arteriole is located anterior to the dorsal root ganglion.

MODE FOR INVENTION

Figure 1:
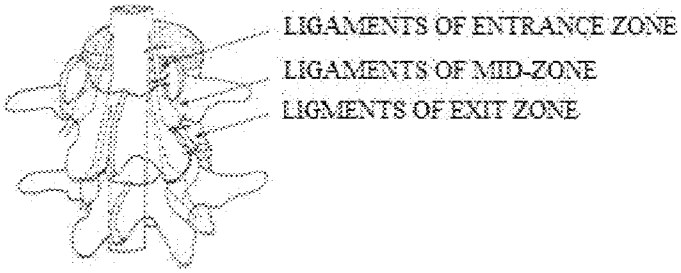
FIG. 1 (prior art)
FIG. 1 is a view illustrating the distribution of ligaments around the intervertebral foramen.
Figure 2:
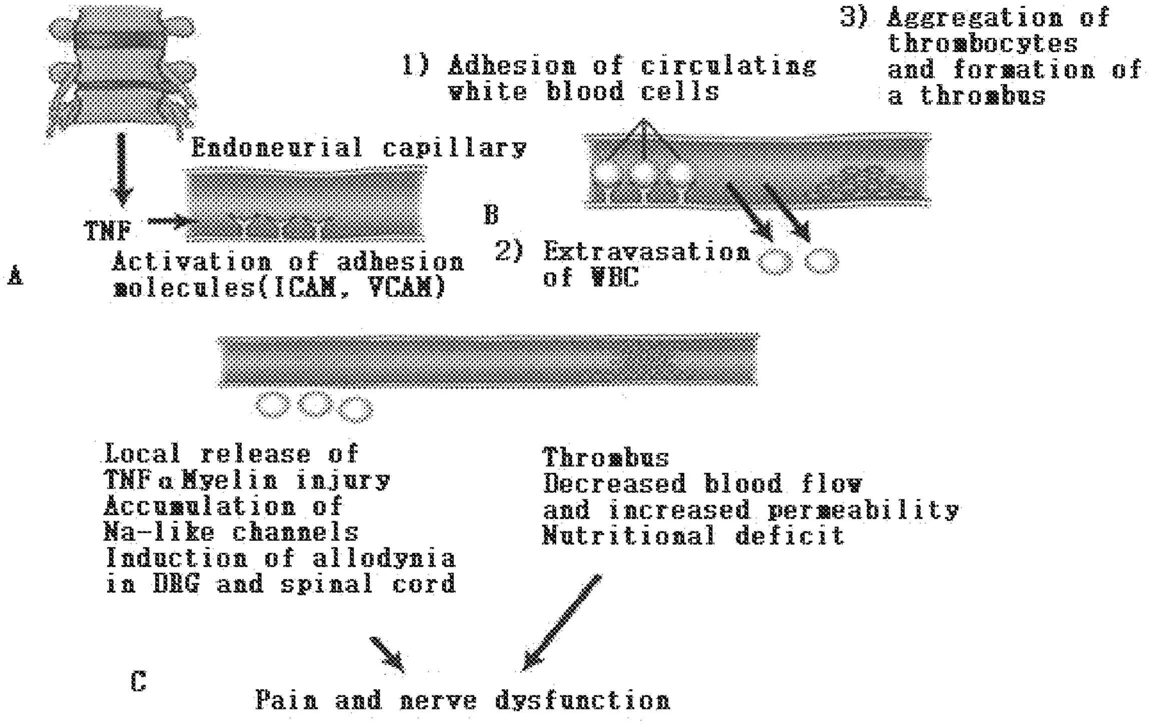
FIG. 2 (prior art)
FIG. 2 is a schematic view showing images for illustrating the process of pain and nerve dysfunction.
Figure 3:
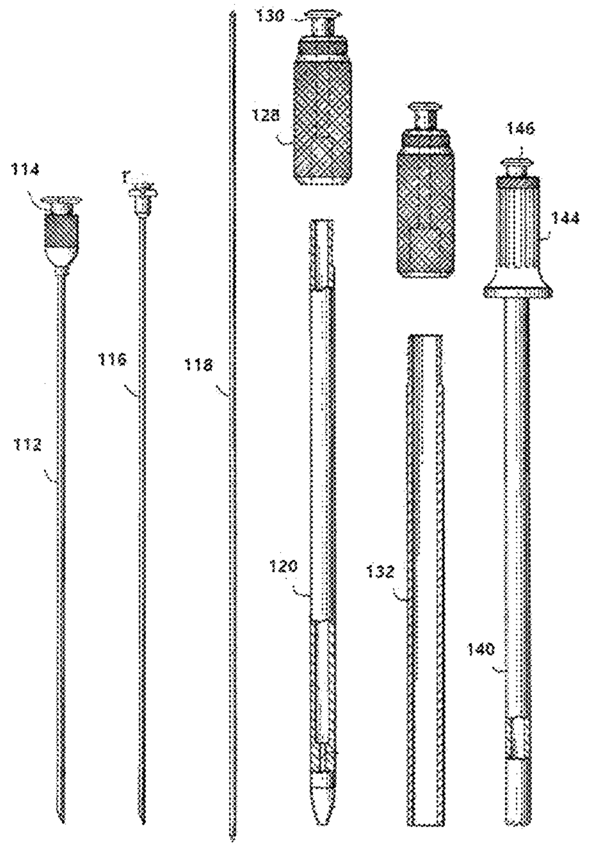
FIG. 3(prior art)
FIG. 3 is a view illustrating the configuration of a tool set for decompression of lumbar herniated intervertebral discs, which is used in the related art.
Figure 5:
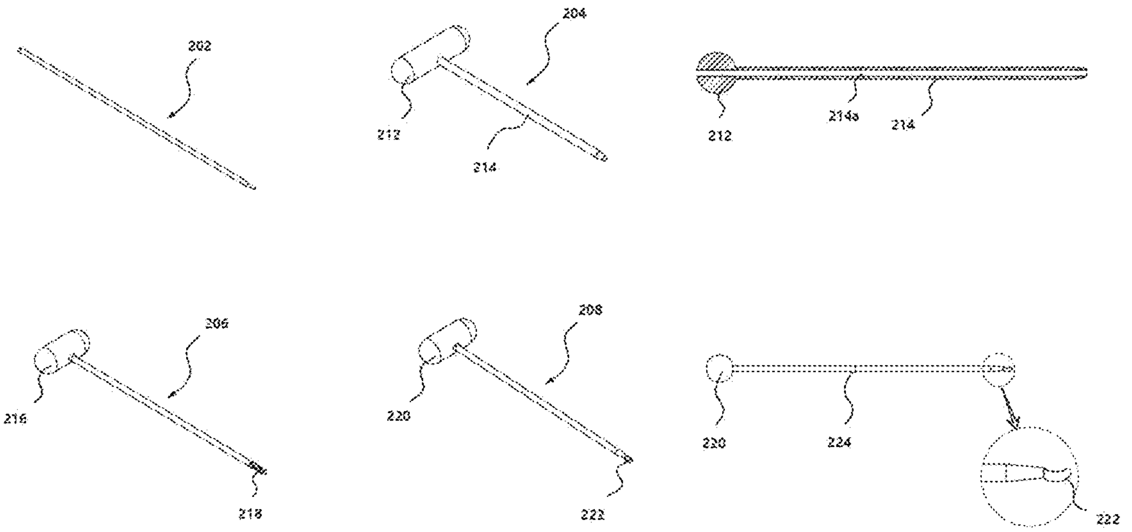
FIG. 5(prior art)
FIG. 5 is a view illustrating the configuration of a tool set according to the related art, which is used for extraforaminotomy.
Figure 6:
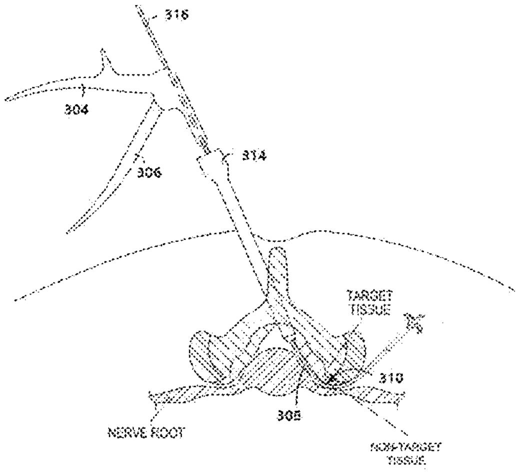
FIG. 6(prior art)
FIG. 6 is a schematic view illustrating a process of removing a ligament from intervertebral foramen according to the related art.

Embodiments of the present invention will be described in detail below with reference to FIGS. 7 to 26.

A tool set for percutaneous extraforaminotomy according to the present invention is configured in such a manner that the straightforward property, the directional property, and the steerable property (switchable directional property) of surgical tools are ensured while the surgical tools are inserted into the spinal facet joint and reach a target point for resection of a ligament surrounding the intervertebral foramen.

The concept of the present invention will be described before delving into preferred embodiments of the present invention.

First, while chemical neurolysis is applied to problems in terms of the inflammatory aspect, mechanical neurolysis or percutaneous extraforaminotomy is applied to solve problems in terms of the mechanical aspect.

The applicant for the present invention has found that back pain or sciatica can be caused by adhesive fibroblasts that had been released from a damaged disc (nucleus pulposus) and cartilage and accumulated around the transforaminal ligament (TFL) of the intervertebral foramen. To eliminate this inflammatory factor causing pain, attempts have been made to employ a percutaneous extraforaminotomy method that inserts surgical tools through the spinal facet joint and performs a resection of the transforaminal ligament of the intervertebral foramen. That is, in the inflammatory aspect rather than the mechanical aspect, the applicant for the present invention has conducted an analysis to identify the physiologic cause of pain and to locate the target point of the inflammatory process, and conducted a clinical study on the anatomical structures of the intervertebral foramen and the transforaminal ligament (TFL) of the intervertebral foramen. The percutaneous extraforaminoctomy, which involves the resection of the transforaminal ligament (TFL) of the intervertebral foramen, importance in biochemical and inflammatory has clinical aspects.

Intervertebral foramen is the passageway to nerve, blood vessels such as veins and arteries, lymphatic vessels, and autonomic nervous systems. Also, DRG (Dorsal Root Ganglion) vulnerable to shock and inflammation is located in the intervertebral foramen and fine ligaments get entangled like a web, so that derivatives caused by inflammatory reactions in the spinal canal are accumulated in the intervertebral foramen. Thus, destructive reactions such as adhesion to nerve tissue, edema caused by inflammation, and obstruction of blood flow to the spinal canal occur in this intervertebral foramen severely and frequently. Therefore, it is the key to the successful surgery to solve the inflammation in the intervertebral foramen and decompress entrapment neuropathy or entrapped part of nerve.

The primary objective of extraforaminotomy, to which the above-mentioned concept applies, is to decompress nerves, as well as to prevent damage to both nerves and blood vessels. Therefore, the functionality of surgical tools is crucial for achieving successful surgery.

A tool set according to one embodiment of the present invention, which is applied to extraforaminotomy, will be described in detail below in terms of a specific shape and functionality thereof with reference to the accompanying drawings.

Figure 7:
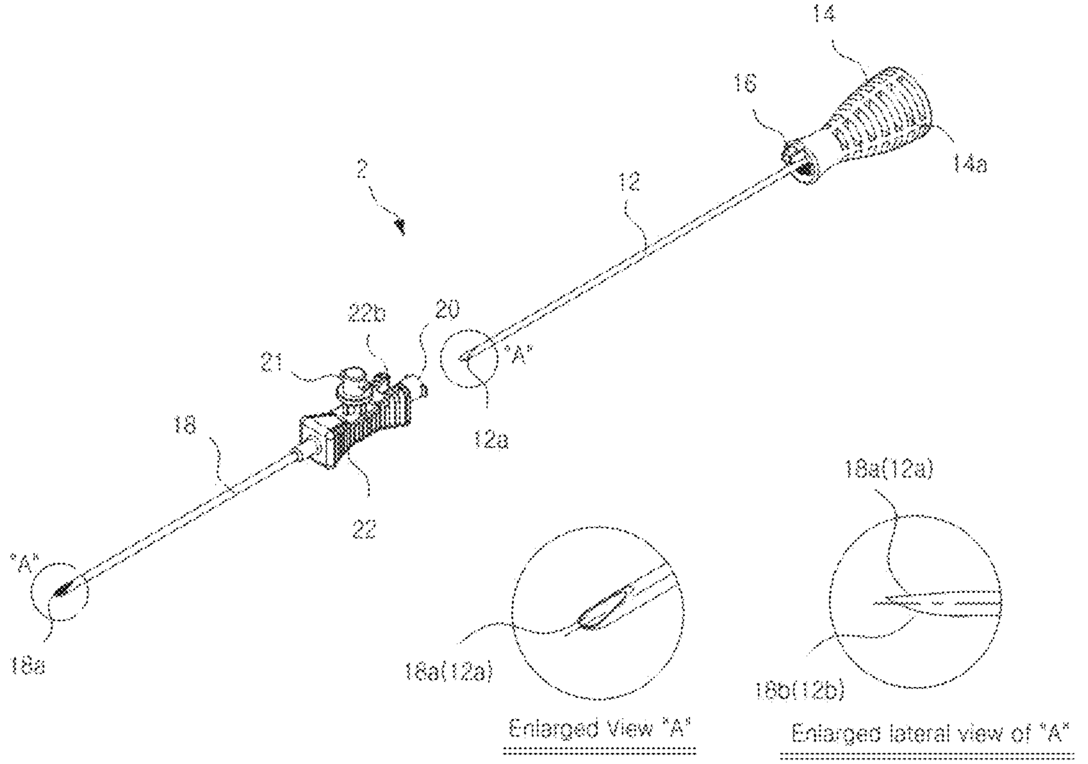
FIG. 7 is an exploded perspective view illustrating a configuration of a stylet member, which is an essential component of a tool set for extraforaminotomy according to a first embodiment of the present invention.
Figure 8:
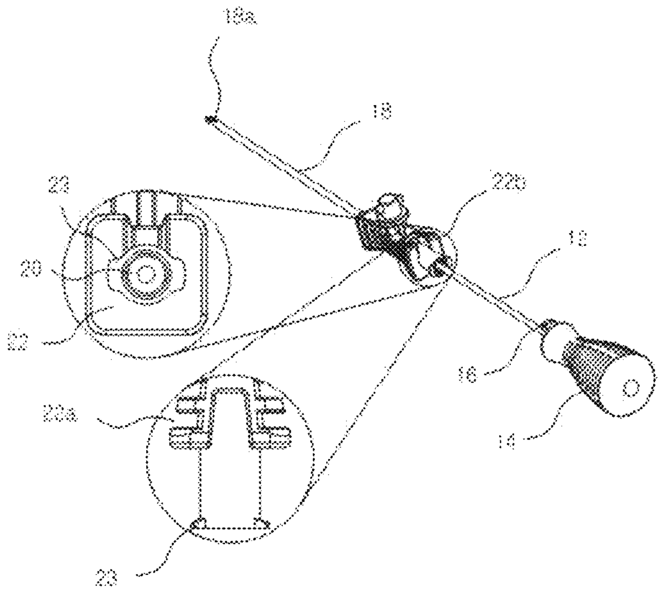
FIG. 8 is an enlarged perspective view illustrating respective coupling portions of a hub and a probe cap of the stylet member in FIG. 7.
Figure 9:
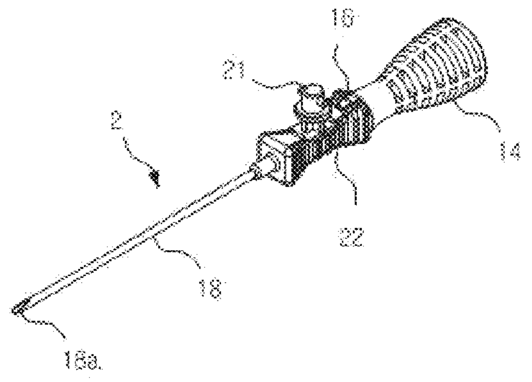
FIG. 9 is a perspective view illustrating that the stylet member in FIG. 7 is assembled.
Figure 10:
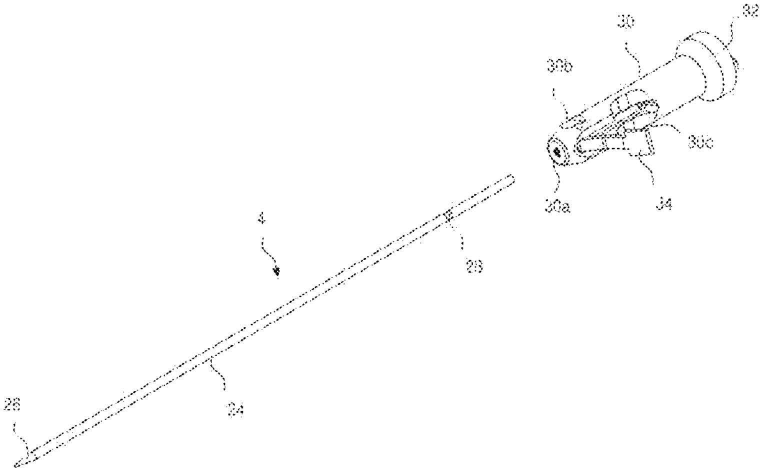
FIG. 10 is an exploded perspective view illustrating a configuration of a trocar, which is an essential component of the tool set for extraforaminotomy according to the first embodiment of the present invention.
Figure 11:
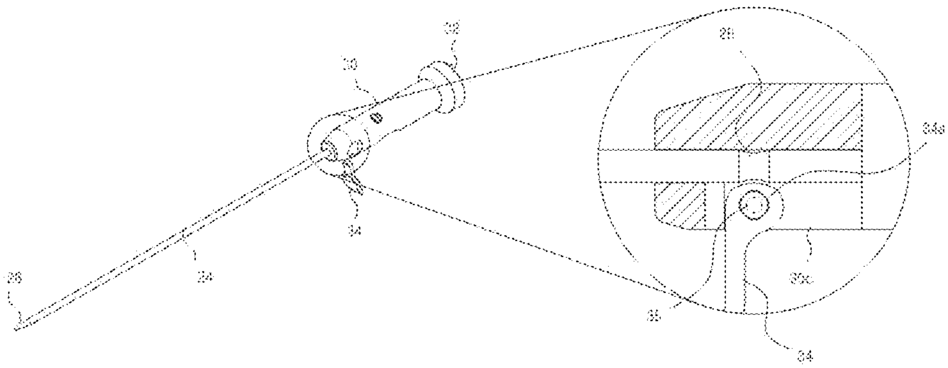
FIGS. 11 and 12 are views that are referenced to describe a process of operating a lever of the trocar illustrated in FIG. 10.
Figure 12:
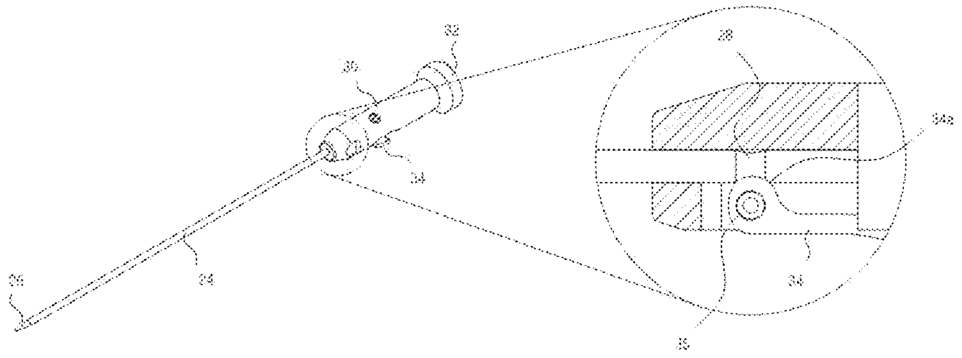
Figure 13:
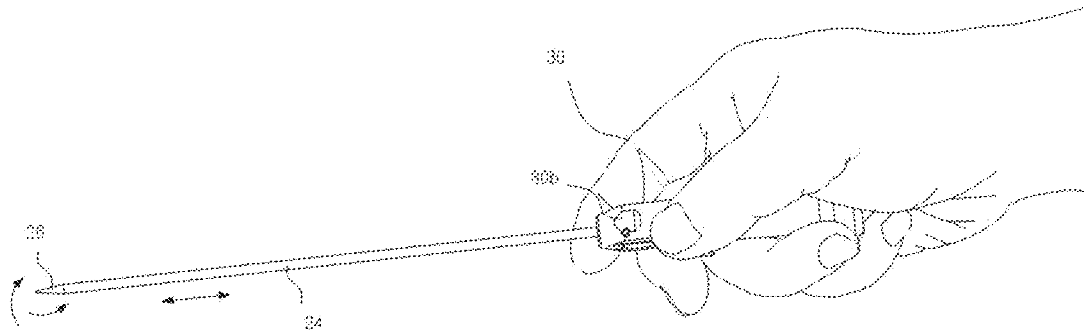
FIG. 13 is a view illustrating a state where a surgical operator grips the trocar on the handle.

FIG. 7 is an exploded perspective view illustrating a configuration of a stylet member, which is an essential component of a tool set for extraforaminotomy according to one embodiment of the present invention; FIG. 8 is an enlarged perspective view illustrating respective coupling portions of a hub and a probe cap of the stylet member shown in FIG. 7; and FIG. 9 is a perspective view illustrating a state in which the stylet member in FIG. 7 is assembled. FIG. 10 is an exploded perspective view illustrating a configuration of a trocar, which is an essential component of the tool set for extraforaminotomy according to one embodiment of the present invention. FIGS. 11 and 12 are views that are referenced to describe a process of operating a lever of the trocar illustrated in FIG. 10. Specifically, FIG. 11 illustrates a state where a pressing portion of a lever is separated from a groove in a probe tip, thereby unlocking the probe tip, and FIG. 12 illustrates a state where the pressing portion of the lever presses against the groove in the probe tip, thereby locking the probe tip. FIG. 13 is a view illustrating a state where a surgical operator grips the handle of the trocar. FIG. 13 is referenced to describe the straightforward property, the directional property, and the steerable property (switchable directional property) of the trocar.

As illustrated in FIGS. 7 to 13, a tool that serves to be preferentially inserted and to reach a target point for resection of a transforaminal ligament in order to perform a resection of the transforaminal ligament of the intervertebral foramen is a stylet member 2. The stylet member 2 includes a probe 12, a mortar-shaped cap 14, a locking lever 16, a guide pipe 18, and a hub 20. The probe 12 has an elongated shape and has a first bevel cut 12*a* at one end thereof. The cap 14 is fixed to the other end of the probe 12 by inserting the other end thereinto and has an outer circumferential surface in which grooves are formed to be spaced a predetermined distance apart from each other. The locking lever 16 is formed on a front end of the cap 14. The guide pipe 18 is formed of an elongated tube in such a manner that the probe 12 is separably inserted thereinto and has a second bevel cut 18*a* at one end thereof. The guide pipe 18, along with the probe 12, percutaneously penetrates the muscular layer and reaches the ligament resection-target point of the intervertebral foramen. The hub 20 is mounted to the other end of the guide pipe 18 and has a hub body 22 having a locking groove 22*b* at one end thereof. The locking groove 22*b* is coupled to the locking lever 16. The hub 20 serves to inject a contrast dye, a pain-relieving medicine, or the like.

The cap 14 and the hub body 22 of the stylet member 2 function as a handle that the surgical operator grips with his/her entire palm in such a manner that the surgical operator can apply a predetermined force to the probe 12 and the guide pipe 18. The functionality of the handle configured by coupling the cap 14 to the hub body 22 provides the straightforward property and the directional property. These properties enable the first and second bevel cuts 12*a* and 18*a*, formed on the probe 12 and the guide pipe 18, respectively, to percutaneously penetrate the muscular layer toward the spinal facet joint and to be inserted in a precisely focused manner toward the ligament resection-target point of the intervertebral foramen.

According to the first embodiment of the present invention, first grooves 14*a* are formed in an outer circumferential surface of the cap 14 in such a manner as to be spaced a predetermined distance apart from each other, and second grooves 22*a* are also formed in an outer circumferential surface of the hub body 22 coupled to the cap 14 in such a manner as to be spaced a predetermined distance apart from each other. The first and second grooves 14*a* and 22*a* serve to provide a better feeling of gripping when the surgical operator applies a predetermined force to the probe 12 and the guide pipe 18 with the cap 14 and the hub body 22 covered with the surgical operator's entire palm. In addition, the first and second grooves 14*a* and 22*a* serve to reduce the weight of the stylet member 2 in such a manner that the weight distribution thereof is not biased toward the rear direction, that is, toward the cap 14. After the probe 12 and the guide pipe 18 reach the ligament resection-target point, a contrast dye is injected into the epidural space through the hub 20, and thus the location of the tip of the guide pipe 18 is identified. Then, when a pain-relieving medicine is injected, the first and second grooves 14*a* and 22*a* function to enable this medicine to be stably injected without the probe 12 and the guide pipe 18 being shaken.

Reference numeral 23 denotes an injection stopper. As illustrated in FIG. 8, the injection stopper functions as a cover wing when a syringe to inject a contrast dye or a pain-relieving medicine is coupled to the guide pipe 18, after the probe 12 is separated from the guide pipe 18. Reference numeral 21 denotes a connector for connection to a navigation antenna or the like.

In addition, as illustrated in FIG. 7, a lower portion opposite to the first bevel cut 12*a* of the probe 12 of the stylet member 2 has a first curved portion 12*b* formed in a round shape. Likewise, a lower portion opposite to the second bevel cut 18*a* of the guide pipe 18 of the stylet member 2 has a second curved portion 18*b* formed in a round shape. In the procedure in which the first and second inclined bevel cuts 12*a* and 18*a* and the first and second curved portions 12*b* and 18*b* percutaneously enter the intervertebral foramen, the first and second curved portions 12*b* and 18*b* is intended for advancing toward the target point while minimizing damage to the nerve or other critical tissues when coming into contact with the nerve or the tissue.

After the ligament resection-target point is first identified through the stylet member, the trocar 4 is then used as a tool that secondarily drills a hole in the ligament. The trocar 4 percutaneously enters the spinal facet joint under the guidance of the guide pipe 18 and reaches a transforaminal ligament resection-target point of the intervertebral foramen. The trocar 4 functions to guide entry of surgical tools described below and, at the same time, serves to primarily perform a resection of the target ligament. According to one embodiment of the present invention, the trocar 4 includes a needle 24 and a first handle 30. The needle 24 is composed of an elongated bar having a groove 28 formed in a predetermined portion thereof and a pointed needle tip 26 at a front end thereof. The first handle 30 is inserted into the needle 24 and can serve to apply a force to ensure the directional property and the straightforward property in accordance with the angle of percutaneous entry to the spinal facet joint.

The first handle 30 has a groove 30*a*, a direction indicating surface 30*b*, and an accommodation space 30*c*. The groove 30*a* is formed in the central portion of the first handle 30. The direction indicating surface 30*b* is formed, as a flat surface, on an upper surface of the front portion of the first handle 30, so that the direction indicating surface 30*b* serves as a reference surface for an entering angle. The accommodation space 30*c* is formed to a predetermined depth into a one-side surface of the first handle 30. A stepped portion 32 for providing a gripping force to the surgical operator is integrally formed with a rear end of the first handle 30. A lever 34 is mounted in the accommodation space 30*c* of the first handle 30, which locks and unlocks the needle 24 according to a rotational operation. The lever 34 is configured to have a pressing portion 34*a* and a shaft 35. The pressing portion 34*a* is formed in a round shape in such a manner as to come into contact with the groove 28 of the needle 24 and to provide a pressing force. The shaft 35 is inserted into the middle of the pressing portion 34*a*, thereby serving as the rotational center.

As illustrated in FIG. 10, when the lever 34 rotates back in the direction vertical to the needle 24, the pressing portion 34*a* is deviated from the grooves 28, thereby freely separating the needle 24. As illustrated in FIG. 11, when the lever 34 is pushed into the accommodation space 30*c* and thereby being accommodated therein, the pressing portion 34*a* is inserted into the groove 28, thereby pressing against the needle 24. Consequently, the needle 24 is held in place.

As illustrated in FIG. 12, while holding onto the first handle 30 with the direction indicating surface 30*b* on the center, the surgical operator causes the trocar 4, configured as described above, to enter, along the guide pipe 18, from the spinal facet joint toward the transforaminal ligament resection-target point of the intervertebral foramen. After the entering of the trocar 4, the guide pipe 18 is removed out. Through these operations, the needle 24 percutaneously penetrates the muscle layer in a smooth manner and enters the intervertebral foramen. In accordance with the angle of percutaneous entry, the first handle 30 provides the directional property and the straightforward property, which can distribute force evenly, in the direction in which the probe tip penetrates. Consequently, these properties can prevent the conventional art problem that the needle 24 is bent, and allow the needle 24 to readily reach the transforaminal ligament resection-target point of the intervertebral foramen.

Figure 14:
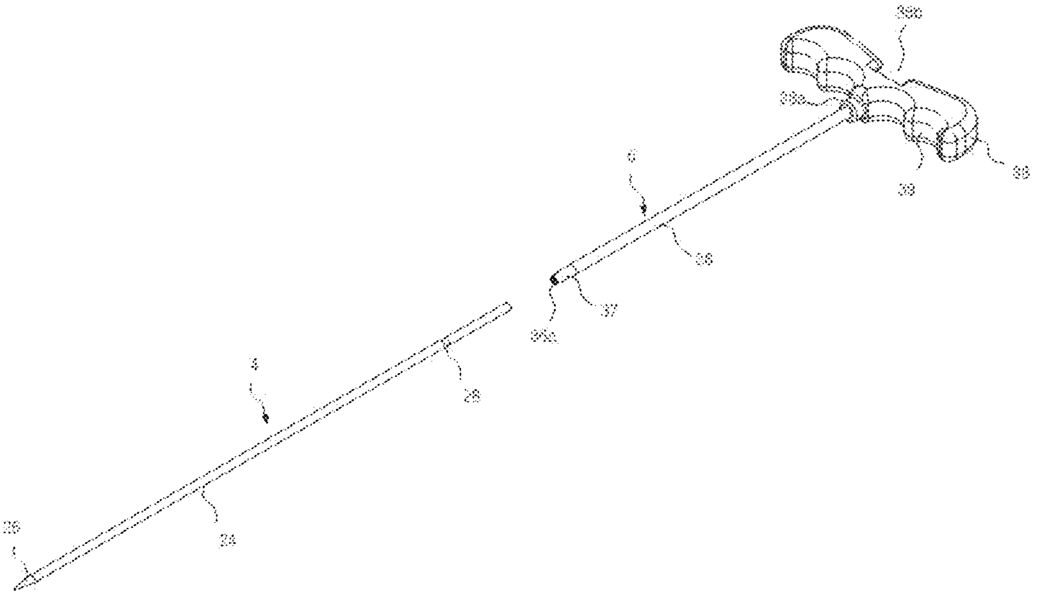
FIG. 14 is an exploded perspective view illustrating coupled configurations of the cannula and the trocar, which is an essential component of the tool set for extraforaminotomy according to the first embodiment of the present invention.
Figure 15:
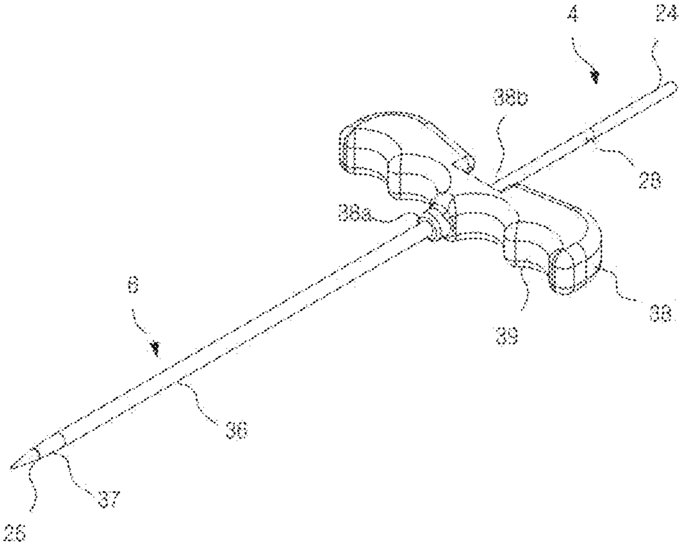
FIG. 15 is a perspective view illustrating a state in which the cannula and the trocar in FIG. 14 are coupled to each other.

FIG. 14 is an exploded perspective view illustrating coupled configurations of the cannula 6 and the trocar 4, which is an essential component of the tool set for extraforaminotomy according to the first embodiment of the present invention. FIG. 15 is a perspective view illustrating a state in which the cannula 6 and the trocar 4 in FIG. 14 are coupled to each other.

After the trocar 4 reaches the transforaminal ligament resection-target point of the intervertebral foramen and a primary resection is completed, the cannula 6, which is to reach the transforaminal ligament resection-target point of the intervertebral foramen under the guidance of the trocar 4, enters. The cannula 6, as illustrated in FIG. 14, includes a sleeve 36 and a handle 38. The sleeve 36 is formed to have a greater diameter than the trocar 4 and has an axial through-hole 36*a* into which the trocar 4 is insertable. The handle 38 has a fixation shaft 38*a* and a seating portion 38*b*. The fixation shaft 38*a* protrudes from the central portion of the handle 38 in such a manner that one end of the sleeve 36 is inserted into the fixation shaft 38*a* to fix the sleeve 36. The seating portion 38*b* is formed on a rear surface of the handle 38. Coupling grooves 38*c* (illustrated in FIG. 17) are formed in both lateral surfaces, respectively, of the seating portion 38*b*. Finger-joint grooves 39 are formed in the handle 38, to the left and the right of the fixation shaft 38*a*, in such a manner that the surgical operator's finger joints are comfortably seated to enhance the feeling of gripping. According to one embodiment of the present invention, a tapered portion 37 that has a gradient is formed in a predetermined section, on the front end portion side, of the sleeve 36. The reason therefor is not only to minimize a gap between the tapered portion and a resection tip of a curette 8 described below and thus to prevent the nerve from being damaged by being caught in the gap during the resection of the transforaminal ligament, but also to facilitate 4 the cannula 6 after percutaneously penetrating the skin.

As illustrated in FIGS. 14 and 15, while holding onto the handle 38, the surgical operator inserts the trocar 4 into the sleeve 36 and then causes the cannula 6, configured as described above, to enter. The sleeve 36 reaches the transforaminal ligament resection-target point of the intervertebral foramen under the guidance of the trocar 4. When the exact resection location is determined, the trocar 4 is separated out from the cannula 6 and removed out.

Figure 16:
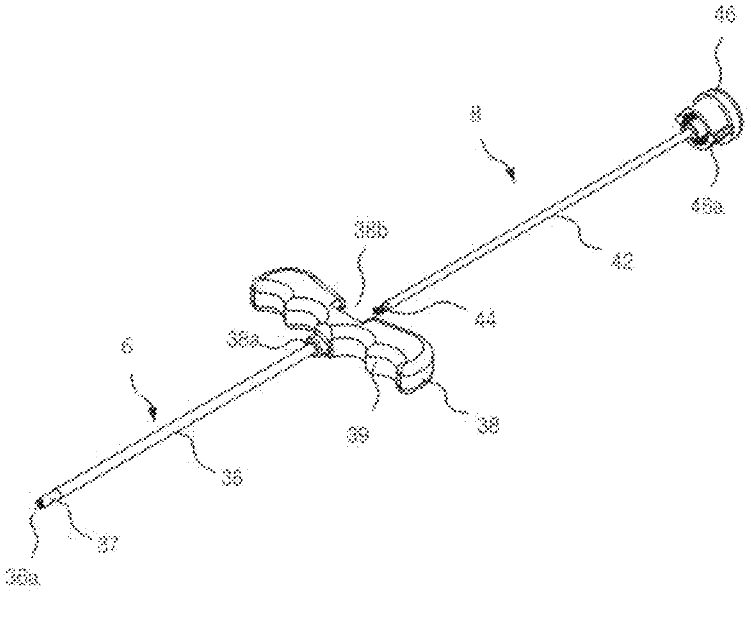
FIG. 16 is a perspective view illustrating coupled configurations of the cannula and the curette, which is an essential component of the tool set for extraforaminotomy according to the first embodiment of the present invention.
Figure 17:
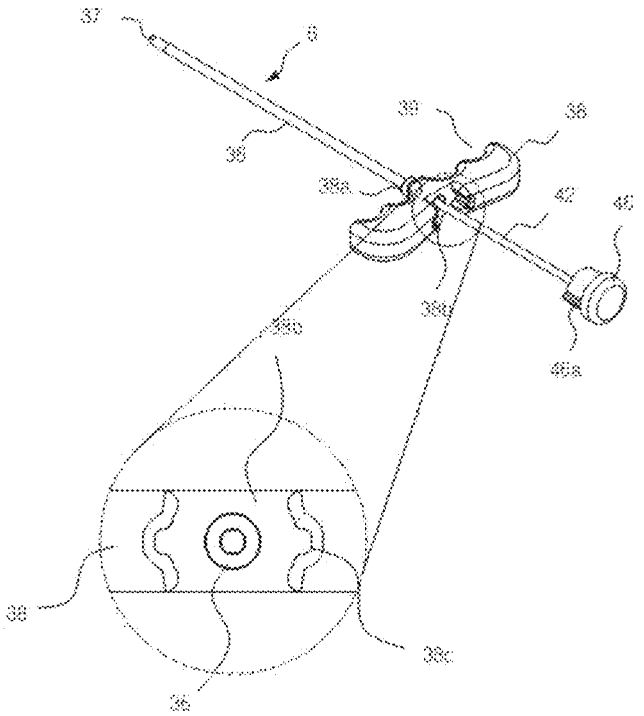
FIG. 17 is a perspective view that is referenced to describe respective coupling portions of the cannula and the curette.
Figure 18:
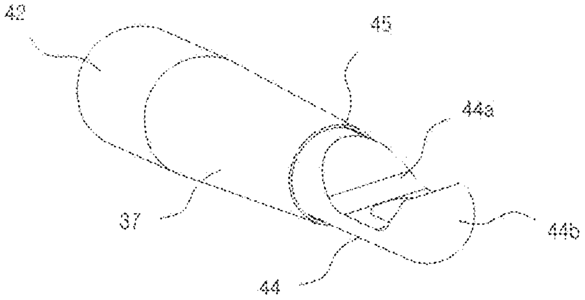
FIG. 18 is a perspective view illustrating a state where a resection tip of the curette according to the present invention is coupled to a tapered portion of the cannula.
Figure 19:
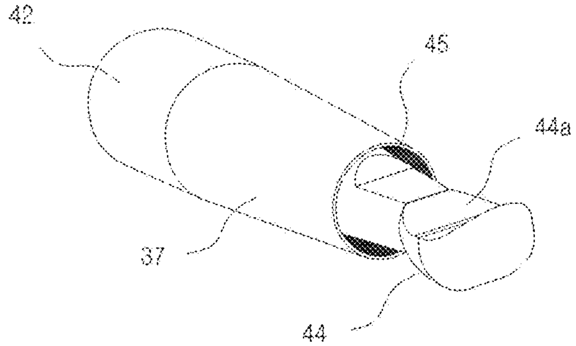
FIG. 19 is an illustrative view that is referenced to describe a structural problem of a gap that occurs in a case where a resection tip is coupled to a tapered portion of a cannula in the related art.
Figure 20A:
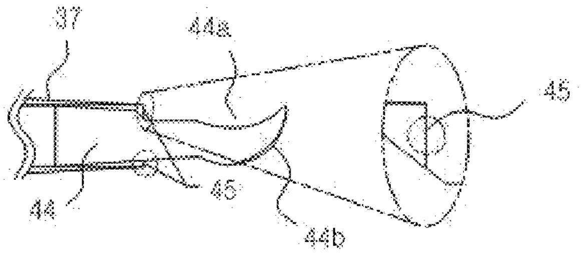
FIGS. 20A and 20B are cross-sectional views illustrating the cannula and the resection tip in the related art and the cannula and resection tip according to the present invention for comparison, respectively, in terms of the gap presence.
Figure 20B:
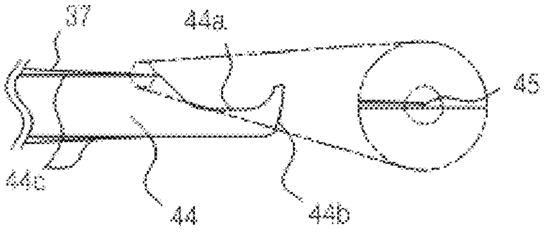
Figure 21:
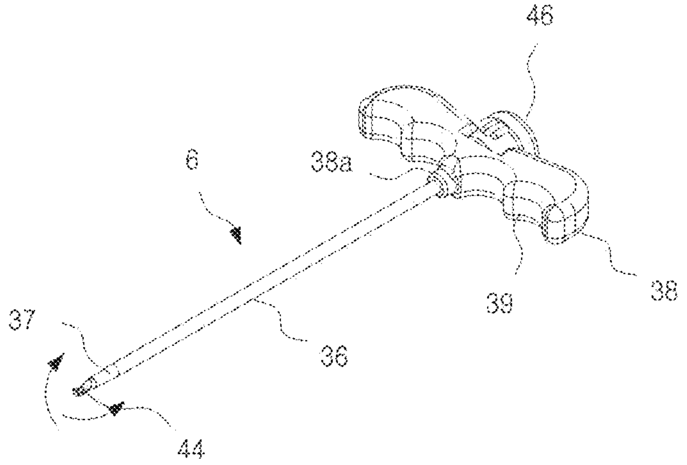
FIG. 21 is a perspective view illustrating the cannula and the curette that are integrally coupled to each other.

FIG. 16 is a perspective view illustrating coupled configurations of the cannula 6 and the curette 8, which is an essential component of the tool set for extraforaminotomy according to one embodiment of the present invention. FIG. 17 is a perspective view that is referenced to describe respective coupling portions of the cannula 6 and the curette 8. FIG. 18 is a perspective view illustrating a state where the resection tip of the curette 8 according to the present invention is coupled to the tapered portion of the cannula 6. FIG. 19 is an illustrative view that is referenced to describe a structural problem of a gap that occurs in a case where a resection tip is coupled to a tapered portion of a cannula in a conventional art. FIGS. 20A and 20B are cross-sectional views illustrating the cannula and the resection tip in a conventional art and the cannula 6 and resection tip according to the present invention for comparison, respectively, in terms of the gap presence. FIG. 20A is a cross-sectional view illustrating a state where the tapered portion of the cannula and the resection tip are coupled to each other according to the related art of FIG. 19. FIG. 20B is a cross-sectional view illustrating that the resection tip of the curette 8 is coupled to the tapered portion of the cannula 6 according to the present invention shown in FIG. 18. FIG. 21 is a perspective view illustrating the cannula 6 and the curette 8 that are integrally coupled to each other.

As illustrated in FIG. 16, the curette 8 is inserted into the cannula 6, and removes the transforaminal ligament spanning across the resection-target point. The curette 8 includes a rod 42, a resection tip 44, and a second handle 46. The rod 42 is inserted into the sleeve 36. The resection tip 44 is provided at a front end of the rod 42 and protrudes out of the tapered portion 37, thereby serving to perform resection of the transforaminal ligament. The second handle 46 is installed at a rear end of the rod 42 and has coupling protrusions 46*a* on both lateral portions, respectively, in such a manner that the coupling protrusions 46*a* are inserted into the coupling grooves 38*c* of the seating portion 38*b* of the cannula 6, respectively.

The resection tip 44 serves to scratch out the transforaminal ligament surrounding the intervertebral foramen. As illustrated in FIGS. 18 and 20B, the resection tip 44 has a concave portion 44*a* with the central portion that curves inward and a rim portion 44*b* formed in a round shape in the periphery of the concave portion 44*a*. The rim portion 44*b* is formed in a round shape to prevent damage to the neuromembrane when coming into contact therewith during resection of the transforaminal ligament. In addition, the resection tip 44 has a straight section 44*c* in such a manner as to come into close contact with an inner surface of the tapered portion 37, having a gradient, of the sleeve 36. Thus, there is almost no gap 45 between respective end portions of the resection tip 44 and the tapered portion 37. According to one embodiment of the present invention, the gap 45 between the respective end portions of the tapered portion 37 and the resection tip 44 has an allowable tolerance ranging from a transition fit to a clearance fit.

As illustrated in FIGS. 19 and 20A, when the gap 45 between the tapered portion 37 and the resection tip 44 occurs as in the related art, the lumbar arteriole or the nerve may be caught in the gap 45, thereby being ruptured. The rupture of the lumbar arteriole causes critical retroperitoneal hematoma. As described above, resection of the ligament is performed in a state where the cannula 6 and the curette 8 are coupled to each other. In the cases where an anomaly may occur that the lumbar arteriole is distributed in a passageway of the transforaminal ligament of the intervertebral foramen, as illustrated in FIG. 18, since there is also almost no gap 45 between the resection tip 44 of the curette 8 and the tapered portion 37 of the cannula 6 (this means that the tolerance ranging from a transition fit to a clearance fit is satisfied) and the resection tip 44 of the curette 8 is formed in a round shape, resection of the ligament can be safely performed without damage to the lumbar arteriole.

Figure 22:
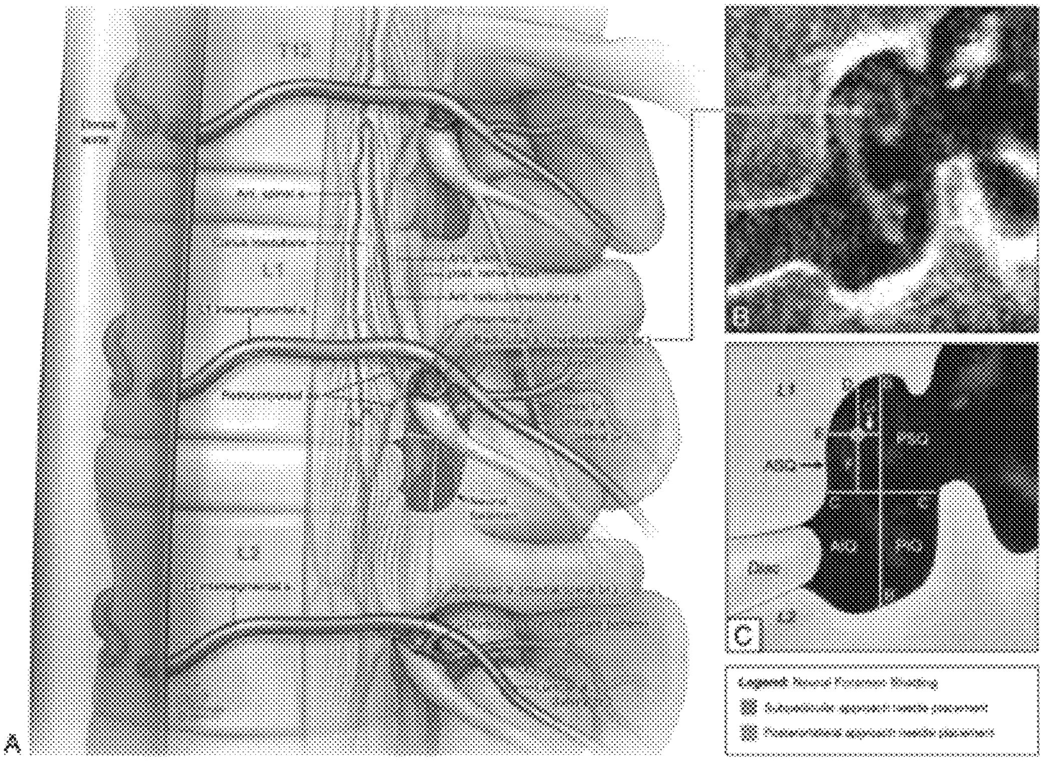
FIG. 22 depicts images showing the position of the lumbar arteriole distributed in the normal aorta.
Figure 23:
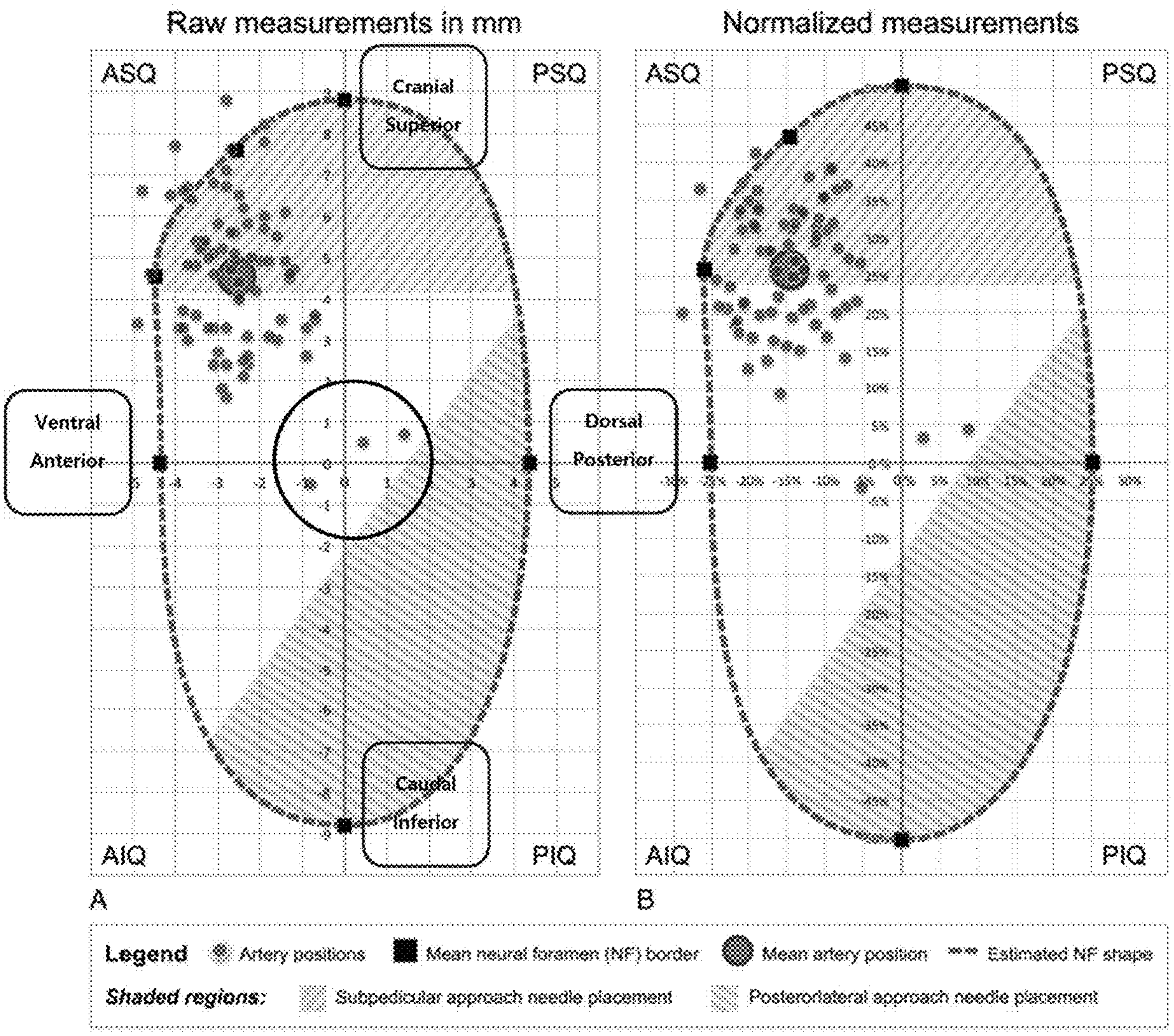
FIG. 23 depicts graphs illustrating the data distribution of the lumbar arteriole, which is measured in a state representing the typical location of the lumbar arteriole.

FIG. 22 depicts images showing the position of the lumbar arteriole distributed in the normal aorta. FIG. 23 depicts graphs illustrating the data distribution of the lumbar arteriole, which is measured in a state representing the typical location of the lumbar arteriole. FIG. 23 illustrates the case where the lumbar arteriole is located posterior to the dorsal root ganglion (refer to the bold black circle in the central portion of the left-side figure), unlike in the typical distribution in which the lumbar arteriole is located anterior to the dorsal root ganglion. The left-side graph in FIG. 23 illustrates raw measurement data, and the right-side graph illustrates normalized measurement data. In addition, the top of the left-side graph corresponds to the cranial direction, the bottom to the caudal direction, the left side to ventral direction, and the right side to the dorsal direction.

With reference to FIGS. 22 and 23, additional descriptions will now be provided. As illustrated in FIG. 22, typically, the lumbar arteriole that branches off from the aorta and enters in a winding manner through the outside of the intervertebral foramen is located anterior to the dorsal root ganglion. That is, as illustrated in the left-side graph in FIG. 23, the solid and gray circle predominantly occupy the central portion of the second quadrant in the upper portion of the left-side graph, representing an average location of the artery. However, when the lumbar arteriole is out of the typical distribution as indicated by the empty bold black circle in the dead center of the left-side graph in FIG. 23, the lumbar arteriole is located posterior to the dorsal root ganglion. This case is referred to as anomaly. In the case of extraforaminotomy, the ligament resection is carried out in such a manner that the ligament is peeled off from bottom to top in the direction from the down-right hatched region, marked "dorsal or posterior," of the left-side graph of FIG. 23 to the left-down hatched region. In a case where during this resection, the lumbar arteriole is found to be present as anomaly, in the structure as illustrated in FIG. 20A, there is a likelihood that the lumbar arteriole will be ruptured by being caught in the gap formed between the respective coupling portions of the tapered portion 37 of the cannula 6 and the resection tip 44 of the curette 8. According to one embodiment of the present invention (see FIGS. 18 and 20B), since there is little or no gap 45 between the respective coupling portions of the tapered portion 37 and the resection tip 44, a phenomenon where the lumbar arteriole is caught in the gap does not occur.

As illustrated in FIG. 21, the rod 42 of the curette 8 configured as described above is inserted into the sleeve 36 of the cannula 6, and the resection tip 44 protrudes out of the tapered portion 37. The second handle 46 of the curette 8 is integrally coupled to the seating portion 38*b* of the cannula 6. Therefore, while holding onto the handle 38 of the cannula 6 integrally coupled to the second handle 46, the surgical operator switches a direction to the upward-downward or the leftward-rightward direction, thereby peeling off the transforaminal ligament and forming a passageway to the intervertebral foramen. The configuration of the curette 8 facilitates the direction switching by peeling off the transforaminal ligament while holding onto the handle 38 of the cannula 6 during the resection of the transforaminal ligament from the intervertebral foramen. The resection tip 44 minimizes damage to the biological tissue located in the vicinity of the target ligament during the resection of the target ligament. In addition, the resection tip 44 performs a resection of the ligaments scratched by the trocar 4 and scrapes the resected ligaments, and pushes out the resected ligaments to the outer wall of the intervertebral foramen, thereby forming an expanded passageway to the intervertebral foramen.

A method of performing percutaneous extraforaminotomy using the tool set, configured as described above, according to one embodiment of the present invention, will be described below with reference to FIGS. 24 to 26.

Figure 24:
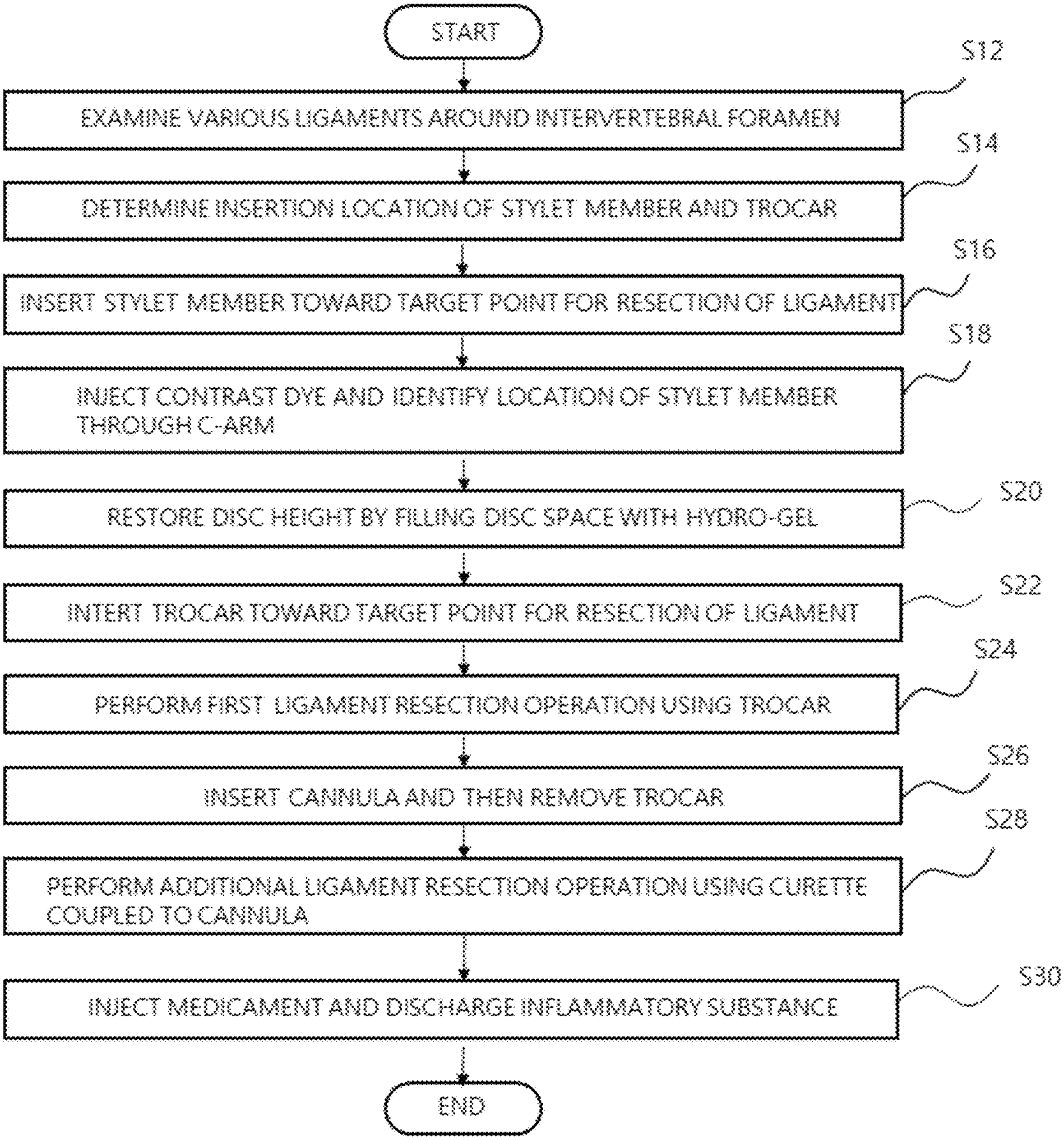
FIG. 24 is a flowchart illustrating a method of performing percutaneous extraforaminotomy using the tool set according to one of the present invention.

FIG. 24 is a flowchart illustrating the method of performing percutaneous extraforaminotomy according to another embodiment of the present invention. The method is performed using the tool set according to one embodiment of the present invention. FIG. 25 depicts photographs illustrating a process in which, a space of the intervertebral foramen is widened, a buckling portion of the capsule surrounding the spinal facet joint stretches out, and the surface of the spinal facet joint becomes smooth (see the gray line portion in FIG. 25) when a disc space is filled with a hydrogel and thus the disc height is restored in Step S20 in FIG. 24. FIG. 26 depicts photographs illustrating a process of filling the disc space with a hydrogel and thus restoring the disc height.

First, various ligaments around the intervertebral foramen are examined before performing percutaneous extraforaminotomy (S12). At this time, an insertion location of the stylet member 2 and the trocar 4 is determined in accordance with a structure of the ligament near the intervertebral foramen which varies among patients (S14). According to the present invention, a target for resection is determined on the intervertebral foramen that is opposite to the disc space connected to one side of the intervertebral foramen. In this case, an edge portion of the intervertebral foramen, which is not in close contact with the dorsal root ganglion (DRG), is a target location. After Step S14, in a state where the probe 12 of the stylet member 2 and the guide pipe 18 are coupled to each other, the guide pipe 18 percutaneously penetrates the muscle layer and is inserted toward the transforaminal ligament resection-target point of the intervertebral foramen (S16). At this time, since the handle is configured by coupling the cap 14 and the hub body 22 to each other, while stably holding onto the handle, the surgical operator can apply a predetermined force to the probe 12 and the guide pipe 18. Thus, the straightforward property and the directional property can be enhanced while the stylet member 2 reaches the ligament resection-target target point of the intervertebral foramen. In addition, since the first grooves 14*a* are formed in the cap 14 in such a manner as to be spaced a predetermined distance apart from each other, and the second grooves 22*a* are formed in the hub body 22 in such a manner as to be spaced a predetermined distance apart from each other, the feeling of gripping and striking the center of weight are enhanced. Accordingly, a contrast dye or a medicine for controlling pain can be stably injected through the hub 20 without being shaken, during the medicine injecting process. The contrast dye is injected into the guide pipe 18 of the stylet member 2, and it is identified whether or not the stylet member 2 is located at the ligament resection-target point (S18).

Subsequently, through a C-arm, the tip of the guide pipe 18 of the stylet member 2 moves toward the disc space while identifying the location of the tip thereof. At this time, through a discogram, the tip of the guide pipe 18 is set to be precisely located within the desired disc space. Subsequently, through the guide pipe 18, after the disc space is filled with a hydrogel, it is checked whether or not the disc height is properly restored (S20). At this point, when the disc height is properly restored, the narrowed space of the intervertebral foramen is also widened at the same time (see FIGS. 25 and 26).

Figure 25:
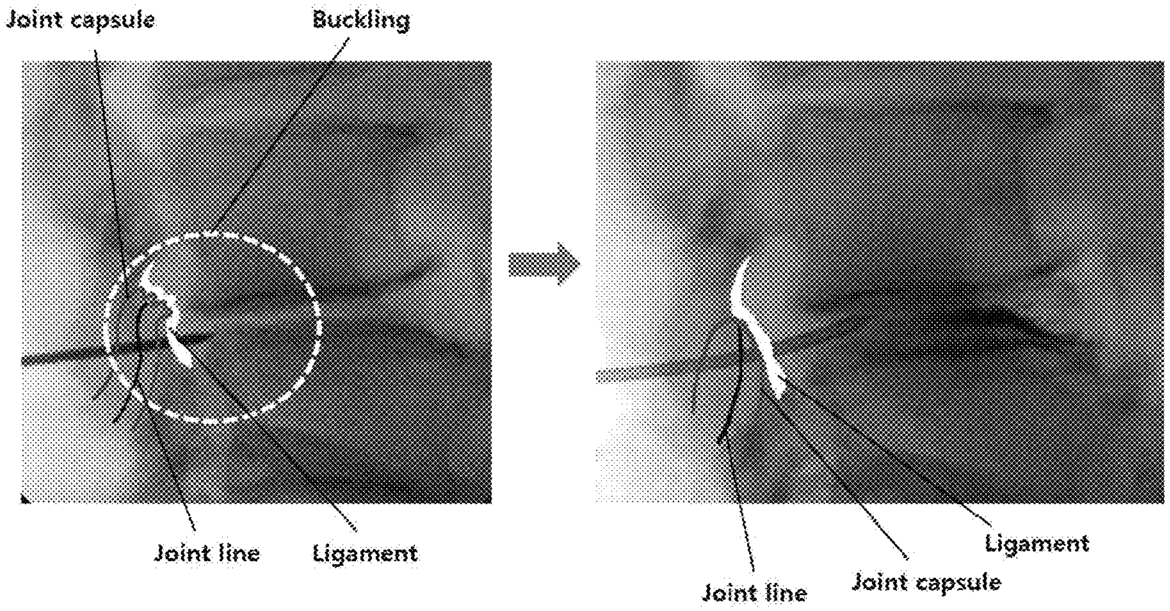
FIG. 25 depicts photographs illustrating a process in which, a space of the intervertebral foramen is widened, a buckling portion of the capsule surrounding the spinal facet joint stretches out, and the surface of the spinal facet joint becomes smooth (see the gray line portion in FIG. 25) when a disc space is filled with a hydrogel and thus the disc height is restored in Step S20 in FIG. 24.
Figure 26:
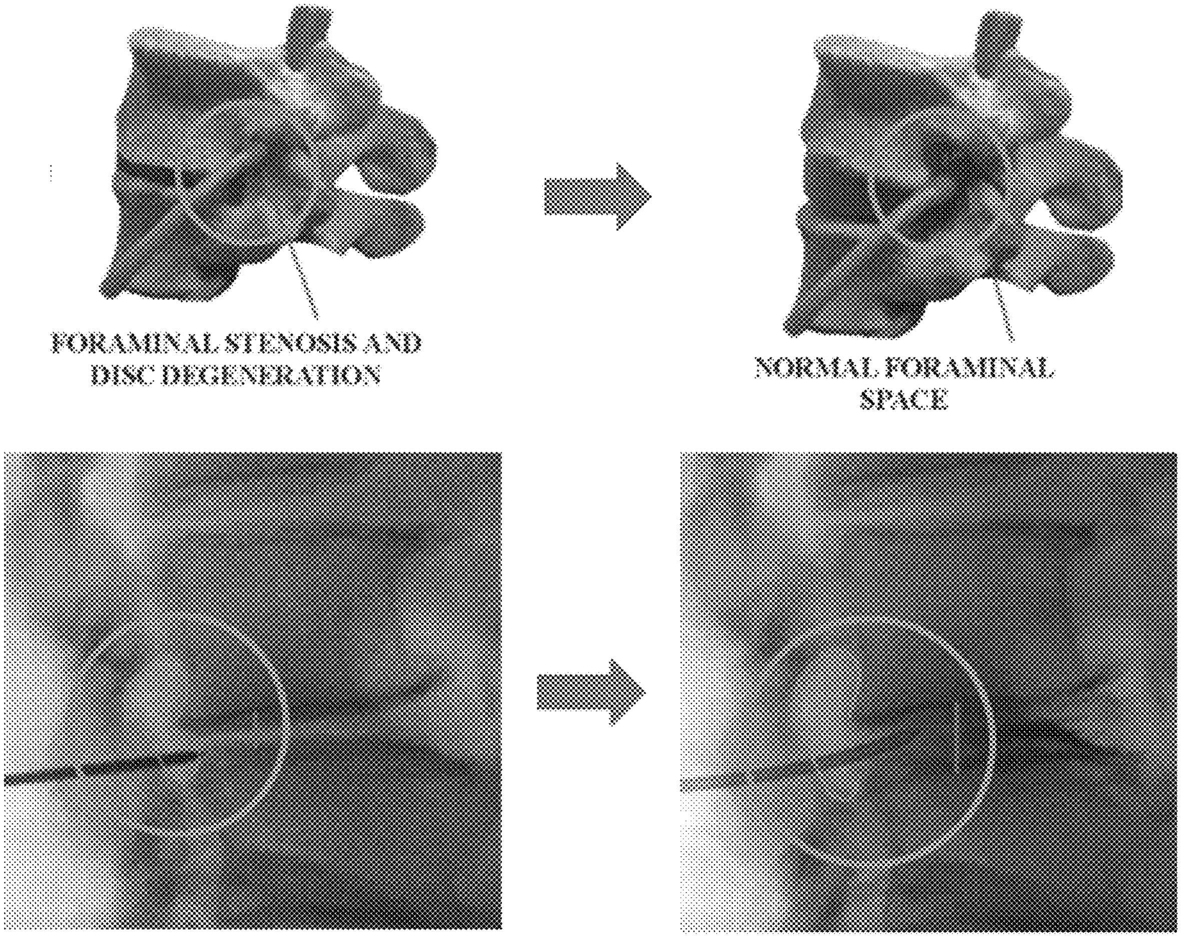
FIG. 26 depicts photographs illustrating a process of filling the disc space with hydro-gel and thus restoring the disc height.

In other words, in Step S20, as illustrated in FIG. 25, a white portion is ligament flavum, the shape of which is marked before (left photo) and after (right photo) injection of a hydrogel for the comparison. The surface of the joint capsule contacted to ligament flavum, the gray line portion of left photo, is marked with the irregular shape. When the disc height is sufficiently restored by filling the disc space with a hydrogel, a space of the intervertebral foramen is also enlarged in the procedure. As a result, the buckling portion of the capsule of the spinal facet joint stretches out and thus the surface of the spinal facet joint becomes smooth. Therefore, during a ligament resection procedure that is performed using the trocar 4 in Step S22 described below, the ligament can be more easily and rapidly resected and peeled away along the joint line while scanning the ligament around the spinal facet joint region from the entry point on the superior articular process through the surface of the spinal facet joint toward the inferior articular process. Thus, the procedure time can be shortened. In addition, sufficient restoration of the disc height can facilitate performing the ligament resection procedure more precisely and safely. FIG. 26 illustrates a comparison between the conditions before and after filling the disc space with the hydrogel and restoring the disc height. FIG. 26 also illustrates a state where the intervertebral foramen changes in size.

After verifying that the disc height has been restored and the space of the intervertebral foramen has been widened, the tip of the guide pipe 18 of the stylet member 2 is set to be relocated at the ligament resection-target point. Next, the trocar 4 is inserted toward the transforaminal ligament resection-target point of the intervertebral foramen through the skin of the portion adjacent to the intervertebral foramen (the spinal facet joint) alongside the inserted guide pipe 18

(S22). In Step S22, through the C-arm, the entrance location of the stylet member 2 and the trocar 4 is also identified.

In the procedure in which the elongated needle 24 of the trocar 4 is caused to enter the resection-target point, since the surgical operator causes the needle 24 to enter toward a determined target location while holding onto the first handle 30, the directionality of the entry angle can be readily adjusted. That is, since the direction indicating surface 30*b* is formed on an upper surface of the first handle 30, the needle 24 can precisely enter in accordance with the entry angle. In addition, since the needle 24 has an elongated shape, when the needle 24 percutaneously penetrates the muscle layer, there is a concern that the needle 24 will be bent. However, as illustrated in FIG. 13, the surgical operator applies a predetermined force to the first handle 30 while pressing against the direction indicating surface 30*b* of the first handle 30, which serves as a reference, with the surgical operator's thumb, and the even distribution of the force can cause the needle 24 to enter without any erroneous direction. Thus, the needle 24 can enter straight without being bent. In addition, in a state where the trocar 4 has reached the resection-target point, a primary resection of the ligament is performed. At this time, the surgical operator peels off the ligament with the feeling that the first handle 30 scans the target point of the intervertebral foramen from downward to upward (S24). That is, the ligament around the spinal facet joint is peeled off from the entry point on the superior articular process through the surface of the spinal facet joint toward the inferior articular process. When this is done, as illustrated in FIG. 13, the surgical operator performs the first primary resection of the ligament using the needle tip 26 while switching the direction from downward to upward (the arrow direction), thus creating a tunnel into the intervertebral foramen.

After of completion 41 the primary resection operation, the sleeve 36 of the cannula 6 is caused to enter, with the needle 24 of the trocar 4 serving as a guiding line in order for a space to be secured for inserting a subsequent tool. Subsequently, the trocar 4 is removed from the sleeve 36 of the cannula 6 (S26).

After the trocar 4 is removed, when the rod 42 of the curette 8 is inserted into the sleeve 36 of the cannula 6, the resection tip 44 protrudes out of the tapered portion 37, thereby being located at the ligament resection-target point. When the curette 8 is inserted into the cannula 6, the second handle 46 of the curette 8 is integrally coupled to the seating portion 38*b* of the handle 38. While holding onto the handle 38 integrally coupled to the second handle 46, the surgical operator switches a direction. Thus, the surgical operator additionally peels off the scratched portion of the ligament attached to the spinal facet joint and scrapes the residue, thereby expanding the passageway to the intervertebral foramen (S28). Subsequently, in a state where the sleeve 36 of the cannula 6 is placed, as is, in the intervertebral foramen, the curette 8 is removed. Finally, through the sleeve 36 of the cannula 6, a catheter is inserted into the intervertebral foramen, and a biochemical substance for controlling pain is suitably delivered to the vicinity of the nerve branches causing pain. Then, an inflammatory substance existing in the spinal canal, with pro-inflammatory materials, is discharged through the expanded intervertebral foramen (S30).

The present invention is not limited to the embodiments described above with reference to the accompanying drawings. It would be obvious to a person of ordinary skill in the art to which the present invention pertains that various substitutions, modifications, and alterations are possible without departing from the technical idea of the present invention.

The invention claimed is:

1. A tool set for percutaneous extraforaminotomy, comprising:

a stylet member comprising an elongated probe, a guide pipe into which the probe is insertable and from which the probe is separable, a cap mounted to the probe, and a hub body mounted to the guide pipe and coupled to the cap;

wherein an end of the probe and an end of the guide pipe each has a bevel cut formed in an inclined shape and a curved portion formed by machining a lower portion opposite to the bevel cut in a round shape, wherein a plurality of grooves are formed in an outer circumferential surface of each of the cap and the hub body, and wherein the stylet member has a handle configured by coupling a locking lever mounted to the cap to a locking groove formed in the hub body, wherein the stylet member reaches a target point for resection of a transforaminal ligament during the percutaneous extraforaminotomy, a trocar comprising a needle having a groove formed in a predetermined portion thereof and a needle tip with a pointed front end, and a first handle inserted into the needle and serving to apply force to the needle in accordance with an angle of percutaneous entry to a spinal facet joint;

wherein the first handle comprises:

a body having a lengthwise groove formed in a central portion thereof and an accommodation space formed in a one-side surface thereof to a predetermined depth, a stepped portion formed at a rear end of the body and serving to provide a gripping force to a surgical operator, a shaft inserted into the accommodation space, and a lever having a pressing portion formed in a round shape to provide a pressing force while coming into contact with the groove of the needle, wherein the shaft is inserted into a center of the pressing portion and is rotatable within the accommodation space to lock and unlock the needle, and wherein the trocar reaches the target point for resection of the transforaminal ligament under guidance of the guide pipe of the stylet member and drills a hole in the transforaminal ligament, during the percutaneous extraforaminotomy, a cannula comprising a sleeve formed to have a greater diameter than that of the trocar and having an axial through-hole into which the trocar is insertable, a fixation shaft located in a central portion of the cannula to insert and fix one end of the sleeve, and a handle having a seating portion formed on a rear surface thereof;

wherein the cannula reaches the target point for resection of the transforaminal ligament under the guidance of the trocar during the percutaneous extraforaminotomy and a curette comprising a rod which is inserted into the sleeve of the cannula, a resection tip provided at a front end of the rod and serving to peel off the transforaminal ligament at the target point, scrape residue of the transforaminal ligament resected primarily, and push the residue into the intervertebral foramen, and a second handle which is seated on the seating portion of the cannula.

2. The tool set of claim 1, wherein the first handle of the trocar further comprises a direction indicating surface formed as a flat surface on an upper surface of a front end portion of the body in such a manner that the surgical operator applies a force to the direction indicating surface using a thumb, wherein the direction indicating surface serves as a reference surface for an entering angle of the needle.

3. The tool set of claim 1, wherein the body further comprises: coupling grooves formed on both sides of a seating portion; and finger-joint grooves formed on both sides of the fixation shaft and serving to enhance a feeling of gripping when the surgical operator's finger joints are placed therein.

4. The tool set of claim 1, wherein a predetermined section at a front-end side of the sleeve of the cannula consists of a tapered portion with a gradient.

5. The tool set of claim 4, further comprising coupling protrusions provided on both sides of the second handle of the curette in such a manner as to be inserted into coupling grooves of the seating portion.

6. The tool set of claim 1, wherein the resection tip of the curette has a central concave portion to scrape the transforaminal ligament surrounding the intervertebral foramen, and a round-shaped rim portion formed at a periphery of the concave portion.

7. The tool set of claim 6, wherein the resection tip has a straight section in such a manner as to come into close contact with an inner surface of the gradient of the tapered portion, and is inserted into and protrudes from the tapered portion of the sleeve, and there is little or no gap between the end of the resection tip and the tapered portion.

8. The tool set of claim 1, wherein a rim portion formed at the resection tip of the curette has a rounded end.

* * * * *